US012169200B2

(12) United States Patent
Lizer et al.

(10) Patent No.: US 12,169,200 B2
(45) Date of Patent: Dec. 17, 2024

(54) LATERAL FLOW DEVICE FOR DETECTING SARS-CoV-2 ANTIBODIES IN HUMAN AND ANIMAL SAMPLES

(71) Applicant: Zoetis Services LLC, Parsippany, NJ (US)

(72) Inventors: Joshua T. Lizer, Augusta, MI (US); Jason J. Workman, Wayland, MI (US); James P. Gillies, Allegan, MI (US); Eric T. Baima, Kalamazoo, MI (US); Rajesh K. Mehra, Hayward, CA (US)

(73) Assignee: Zoetis Services LLC, Parsippany, NJ (US)

( * ) Notice: Subject to any disclaimer, the term of this patent is extended or adjusted under 35 U.S.C. 154(b) by 309 days.

(21) Appl. No.: 17/389,473

(22) Filed: Jul. 30, 2021

(65) Prior Publication Data

US 2022/0050102 A1 Feb. 17, 2022

Related U.S. Application Data

(60) Provisional application No. 63/064,225, filed on Aug. 11, 2020.

(51) Int. Cl.
*G01N 33/543* (2006.01)
*G01N 33/569* (2006.01)

(52) U.S. Cl.
CPC . *G01N 33/54388* (2021.08); *G01N 33/56983* (2013.01); *G01N 2333/165* (2013.01)

(58) Field of Classification Search
None
See application file for complete search history.

(56) References Cited

U.S. PATENT DOCUMENTS

| | | | |
|---|---|---|---|
| 10,823,746 | B1 | 11/2020 | Busa et al. |
| 10,948,490 | B1 | 3/2021 | Van Der Werf et al. |
| 11,021,531 | B1 | 6/2021 | Glanville et al. |
| 2021/0024998 | A1 | 1/2021 | Lamble et al. |
| 2021/0190797 | A1 | 6/2021 | Messing et al. |
| 2021/0277092 | A1 | 9/2021 | Crowe, Jr. et al. |
| 2021/0291165 | A1 | 9/2021 | Rothberg et al. |
| 2021/0300999 | A1 | 9/2021 | Crowe, Jr. et al. |
| 2021/0302436 | A1 | 9/2021 | Rai et al. |
| 2021/0304856 | A1 | 9/2021 | Miller et al. |
| 2021/0311036 | A1 | 10/2021 | Lapointe et al. |
| 2021/0319904 | A1 | 10/2021 | Hall et al. |
| 2021/0325390 | A1 | 10/2021 | Bell |

FOREIGN PATENT DOCUMENTS

| | | | |
|---|---|---|---|
| EP | 3 910 332 | A1 | 11/2021 |
| WO | WO 2021/007357 | A1 | 1/2021 |
| WO | WO 2021/076841 | A1 | 4/2021 |
| WO | WO 2021/086544 | A1 | 5/2021 |
| WO | WO 2021/097193 | A1 | 5/2021 |
| WO | WO 2021/156878 | A2 | 8/2021 |
| WO | WO 2021/163608 | A2 | 8/2021 |
| WO | WO 2021/176378 | A1 | 9/2021 |
| WO | WO 2021/181338 | A1 | 9/2021 |
| WO | WO 2021/186081 | A1 | 9/2021 |
| WO | WO 2021/188395 | A1 | 9/2021 |
| WO | WO 2021/195023 | A2 | 9/2021 |
| WO | WO 2021/195420 | A1 | 9/2021 |
| WO | WO 2021/202158 | A1 | 10/2021 |
| WO | WO 2021/202992 | A2 | 10/2021 |
| WO | WO 2021/203103 | A2 | 10/2021 |
| WO | WO 2021/205042 | A1 | 10/2021 |
| WO | WO 2021/205228 | A1 | 10/2021 |
| WO | WO 2021/207209 | A2 | 10/2021 |
| WO | WO 2021/211331 | A1 | 10/2021 |
| WO | WO 2021/212104 | A1 | 10/2021 |
| WO | WO 2021/216276 | A1 | 10/2021 |
| WO | WO 2021/216573 | A1 | 10/2021 |
| WO | WO 2021/216983 | A1 | 10/2021 |
| WO | WO 2021/217032 | A2 | 10/2021 |
| WO | WO 2021/222597 | A2 | 11/2021 |
| WO | WO 2021/222610 | A2 | 11/2021 |
| WO | WO 2021/222878 | A1 | 11/2021 |
| WO | WO 2021/224493 | A1 | 11/2021 |
| WO | WO 2021/226229 | A1 | 11/2021 |
| WO | WO 2021/226278 | A1 | 11/2021 |

(Continued)

OTHER PUBLICATIONS

Sotnikov, et al. Sensors (Basel). Dec. 25, 2017;18(1):36. doi: 10.3390/s18010036. PMID: 29295582. (Year: 2017).*
Kontou, et al. Diagnostics (Basel). May 19, 2020;10(5):319. doi: 10.3390/diagnostics10050319. PMID: 32438677. (Year: 2020).*
Koczula, et al. Essays Biochem. Jun. 30, 2016;60(1):111-20. doi: 10.1042/EBC20150012. PMID: 27365041. (Year: 2016).*
Hsieh, et al. bioRxiv [Preprint]. May 30, 2020:2020.05.30.125484. doi: 10.1101/2020.05.30.125484. Update in: Science. Jul. 23, 2020;: PMID: 32577660. (Year: 2020).*
Anfossi, et al. Anal Bioanal Chem. Jul. 2018;410(17):4123-4134. doi: 10.1007/s00216-018-1067-x. Epub Apr. 23, 2018. PMID: 29687248. (Year: 2018).*
Pal, et al. Cureus. Mar. 26, 2020;12(3):e7423. doi: 10.7759/cureus.7423. PMID: 32337143. (Year: 2020).*
Tian, et al. Potent binding of 2019 novel coronavirus spike protein by a SARS coronavirus-specific human monoclonal antibody. Emerg Microbes Infect. Feb. 17, 2020;9(1):382-385. doi: 10.1080/22221751.2020.1729069. PMID: 32065055. (Year: 2020).*

(Continued)

*Primary Examiner* — Benjamin P Blumel
*Assistant Examiner* — Jeffrey Mark Sifford
(74) *Attorney, Agent, or Firm* — Gloria K. Szakiel

(57) ABSTRACT

The invention provides a lateral flow device and methods for the detection of antibodies to severe acute respiratory syndrome coronavirus 2 (SARS-CoV-2) in a sample of bodily fluid of an animal or human. The test methods include contacting the sample with a conjugate comprising a recombinant SARS-CoV-2 spike protein antigen that has been conjugated to a detection agent, wherein an antigen-antibody complex is formed between the SARS-CoV-2 spike protein antigen conjugate and SARS-CoV-2 antibodies present in the sample; capturing the formed antigen-antibody complex with an Fc-binding molecule; and detecting the captured complex.

26 Claims, 4 Drawing Sheets

Specification includes a Sequence Listing.

(56) References Cited

FOREIGN PATENT DOCUMENTS

| | | | |
|---|---|---|---|
| WO | WO 2021/228092 | A1 | 11/2021 |
| WO | WO 2021/250467 | A2 | 12/2021 |

OTHER PUBLICATIONS

Won Lee, et al., "Clinical Evaluation of a COVID-19 Antibody Lateral Flow Assay using Point of Care Samples," MedRxiv: the Preprint Server for Health Sciences, Dec. 4, 2020, pp. 1-18.
Amanda Haymond, et al., "Clinical Utility of a Highly Sensitive Lateral Flow Immunoassay as determined by Titer Analysis for the Detection of anti-SARS-CoV-2 Antibodies at the Point-of-Care," MedRxiv: the Preprint Server for Health Sciences. Aug. 2, 2020, pp. 1-43.
Steven E. Conklin, et al., "Evaluation of Serological SARS-CoV-2 Lateral Flow Assays for Rapid Point of Care Testing," MedRxiv: the Preprint Server for Health Sciences. Aug. 4, 2020, pp. 1-27.
Suzanne Pickering, et al., "Comparative assessment of multiple COVID-19 serological technologies supports continued evaluation of point-of-care lateral flow assays in hospital and community healthcare settings," PLOS Pathogens, Sep. 24, 2020, pp. 1-19.
Tian Wen, et al., "Development of a lateral flow immunoassay strip for rapid detection of IgG antibody against SARS-CoV-2 virus," Analyst, 2020, 145 (15), pp. 5345-5352.
Thomas Nicol, et al., "Assessment of SARS-CoV-2 serological tests for the diagnosis of COVID-19 through the evaluation of three immunoassays: Two automated immunoassays (Euroimmun and Abbott) and one rapid lateral flow immunoassay (NG Biotech)," Journal of Clinical Virology, 129 (2020) 104511, pp. 1-7.
Francisco Javier Candel González, et al., "Utility of lateral flow tests in SARS-CoV-2 infection Monitorization," Revista Espanola de Quimioterapia. 33(4):258-266, Jun. 4, 2020.
Barnaby Flower, et al., "Clinical and laboratory evaluation of SARS-CoV-2 lateral flow assays for use in a national COVID-19 seroprevalence survey," Thorax 2020;0:1-7. doi:10.1136/thoraxjnl-2020-215732.
Daming Wang, et al., "Rapid lateral flow immunoassay for the fluorescence detection of SARS-CoV-2 RNA," Nature Biomedical Engineering, vol. 4, Dec. 2020, pp. 1150-1158.
Jhong-Lin Wu, et al., "Four point-of-care lateral flow immunoassays for diagnosis of COVID-19 and for assessing dynamics of antibody responses to SARS-CoV-2," Journal of Infection, 81 (2020), pp. 435-442.
Isabel Montesinos, et al., "Evaluation of two automated and three rapid lateral flow immunoassays for the detection of anti-SARS-CoV-2 antibodies," Journal of Clinical Virology, 128 (2020), 104413, pp. 1-6.
R. Patil, et al., "An In-House Lateral Flow Immunoassay: Point of Care Test for Covid-19 IGG/IGM Antibodies Detection," Indian Journal of Hematology Blood Transfusion (Nov. 2020) 36 (Suppl 1), S1-S229. p. S114 Conference: 61st Annual Conference of Indian Society of Hematology and Blood Transfusion (ISHBT) Nov. 2020.
Tao Peng, et al., "Enhancing sensitivity of lateral flow assay with application to SARS-CoV-2," Applied Physics Letters, 117, pp. 120601-1-120601-4 (2020).
Moïse Michel, et al., "Evaluating ELISA, Immunofluorescence, and Lateral Flow Assay for SARS-CoV-2 Serologic Assays," Frontiers in Microbiology. 11:597529, Dec. 11, 2020, pp. 1-8.
Chao Huang, et al., "Rapid Detection of IgM Antibodies against the SARS-CoV-2 Virus via Colloidal Gold Nanoparticle-Based Lateral-Flow Assay," ACS Omega, 5, pp. 12550-12556, 2020.
Shey-Ying Chen, et al., "Multicenter evaluation of two chemiluminescence and three lateral flow immunoassays for the diagnosis of COVID-19 and assessment of antibody dynamic responses to SARS-CoV-2 in Taiwan," Emerging Microbes & Infections, 2020, vol. 9, pp. 2157-2168.
Benjamin D. Grant, et al. "SARS-CoV-2 Coronavirus Nucleocapsid Antigen-Detecting Half-Strip Lateral Flow Assay Toward the Development of Point of Care Tests Using Commercially Available Reagents," Analytical Chemistry 2020, 92(16), pp. 11305-11309, Jul. 1, 2020.
Zhenhua Chen, et al., "Rapid and Sensitive Detection of anti-SARS-CoV-2 IgG, Using Lanthanide-Doped Nanoparticles-Based Lateral Flow Immunoassay," Analytical Chemistry, 2020, 92(10): pp. 7226-7231.
Carmen L. Charlton, et al. "Evaluation of Six Commercial Mid-to High-Volume Antibody and Six Point-of-Care Lateral Flow Assays for Detection of SARS-CoV-2 Antibodies," Journal of Clinical Microbiology, vol. 58, Issue 10, Jul. 14, 2020, pp. 1-12.
Brett Ragnesola, et al., "COVID19 antibody detection using lateral flow assay tests in a cohort of convalescent plasma donors," BMC Research Notes (2020) 13:372, pp. 1-7.
Chongwen Wang, et al., "Sensitive and Simultaneous Detection of SARS-CoV-2-Specific IgM/IgG Using Lateral Flow Immunoassay Based on Dual-Mode Quantum Dot Nanobeads," Analytical Chemistry, 2020, 92, pp. 15542-15549.
Maria Martínez Serrano, et al., "Comparison of commercial lateral flow immunoassays and ELISA for SARS-CoV-2 antibody detection," Journal of Clinical Virology 129 (2020) 104529, pp. 1-4.
Felipe Perez-García, et al., "Alltest rapid lateral flow immunoassays is reliable in diagnosing SARS-CoV-2 infection from 14 days after symptom onset: a prospective single-center study," Journal of Clinical Virology 129 (2020) 104473, pp. 1-5.
Antonio Russo, et al., "Assessment and Comparison of Two Serological Approaches for the Surveillance of Health Workers Exposed to SARS-CoV-2," Infection and Drug Resistance 13:4501-4507, 2020.
Zahra Riktegaran Tehrani, et al., "Performance of nucleocapsid and spike-based SARS-CoV-2 serologic assays," PLoS ONE [Electronic Resource]. 15(11):e0237828, Nov. 2, 2020, pp. 1-12.
Jeffrey D. Whitman et al., "Test performance evaluation of SARS-CoV-2 serological assays," Nature Biotechnology, Oct. 2020; 38(10):1174-1183, pp. 1-26.
Alexis C.R. Hoste, et al., "Two serological approaches for detection of antibodies to SARS-CoV-2 in different scenarios: a screening tool and a point-of-care test," Diagnostic Microbiology and Infectious Disease 98 (2020) 115167, pp. 1-5.
Li-Xia Zhang, et al., "Preliminary Analysis of B- and T-Cell Responses to SARS-CoV-2," Molecular Diagnosis & Therapy (2020) 24(5):601-609.
Caterina Maria Gambino, et al., "Comparison of a rapid immunochromatographic test with a chemiluminescence immunoassay for detection of anti-SARS-CoV-2 IgM and IgG," Biochemia Medica. (Zagreb) 2020; 30(3):030901, pp. 1-6.
Andrea P. Espejo, MD, et al., "Review of Current Advances in Serologic Testing for COVID-19," American Journal of Clinical Pathology, 2020; 154: pp. 293-304.
Zahra Rikhtegaran Tehrani, et al., "Specificity and Performance of Nucleocapsid and Spike-based SARS-CoV-2 Serologic Assays," MedRxiv: the Preprint Server for Health Sciences, Aug. 7, 2020, pp. 1-12.
Emily R. Adams, et al., "Antibody testing for COVID-19: a report from the National COVID Scientific Advisory Panel," Wellcome Open Research 2020, 5:139, pp. 1-17.
Angela Chiereghin, et al., "Recent Advances in the Evaluation of Serological Assays for the Diagnosis of SARS-CoV-2 Infection and COVID-19," Frontiers in Public Health, vol. 8, Article 620222, 2020, pp. 1-9.
Pedro C. Hallal, et al., "SARS-CoV-2 antibody prevalence in Brazil: results from two successive nationwide serological household surveys," The Lancet Global Health, vol. 8(11):e1390-e1398, Sep. 23, 2020
Marzia Nuccetelli, et al., "Combined anti-SARS-CoV-2 IgA, IgG, and IgM Detection as a Better Strategy to Prevent Second Infection Spreading Waves," Immunological Investigations, pp. 1-13, Sep. 18, 2020.
Melkon G. Dombourian, et al., "Analysis of COVID-19 convalescent plasma for SARS-CoV-2 IgG using two commercial immunoassays," Journal of Immunological Methods, 486 (Aug. 20, 2020) 112837, pp. 1-5.

(56) References Cited

OTHER PUBLICATIONS

Jeffrey D. Whitman, et al., "Test performance evaluation of SARS-CoV-2 serological assays," MedRxiv: the Preprint Server for Health Sciences, May 17, 2020, pp. 1-28.
Niko Kohmer, et al., "Clinical performance of different SARS-CoV-2 IgG antibody Tests," Journal of Medical Virology, 2020;92, pp. 2243-2247.
Deeks JJ, et al., "Antibody tests for identification of current and past infection with SARS-CoV-2," Cochrane Database of Systematic Reviews, 2020, Issue 6, Art No. CD013652, pp. 1-306.
Steven Riley, et al., "REal-time Assessment of Community Transmission (REACT) of SARS-CoV-2 virus: Study protocol," Wellcome Open Research 2020, 5:200, pp. 1-17.
Ismael Amaral Silva P.A., et al., "Universal screening of SARS-CoV-2 of oncology healthcare workers—a Brazilian experience," Annals of Oncology. Conference: ESMO Virtual Congress 2020. Virtual, Online. 31(Supplement 4) (pp. S1024), 2020. Date of Publication: Sep. 2020.
Susanna K. Elledge, et al., "Engineering luminescent biosensors for point-of-care SARS-CoV-2 antibody detection," MedRxiv : the Preprint Server for Health Sciences. Aug. 21, 2020.
Anwar M. Hashem, et al., "Performance of Commercially Available Rapid Serological Assays for the Detection of SARS-CoV-2 Antibodies," Pathogens. 9(12), Dec. 19, 2020, pp. 1-10.
Gláucia Cota, et al., "Diagnostic performance of commercially available COVID-19 serology tests in Brazil," International Journal of Infectious Diseases, 101 (2020), pp. 382-390.
J. Van Elslande, et al., "Diagnostic performance of seven rapid IgG/IgM antibody tests and the Euroimmun IgA/IgG ELISA in COVID-19 patients," Clinical Microbiology and Infection 26 (2020), pp. 1082-1087.
Martin Risch, et al., "Temporal Course of SARS-CoV-2 Antibody Positivity in Patients with COVID-19 following the First Clinical Presentation," BioMed Research International, vol. 2020, Article ID 9878453, pp. 1-12.
Zhizeng Wang, et al., "A point-of-care selenium nanoparticle-based test for the combined detection of anti-SARS-CoV-2 IgM and IgG in human serum and blood," Lab on a Chip, 2020, 20, pp. 4255-4261.
R.L. Dewar, et al., "Comparative assessment of multiple SARS-CoV-2 antibody and neutralization assays from blood samples in COVID-19 infected patients," Open Forum Infectious Diseases. Conference: Infectious Diseases Week, IDWeek 2020. Virtual. 7(SUPPL 1) (pp. S276), 2020. Date of Publication: Dec. 31, 2020.
Panagiota I. Kontou, et al., "Antibody Tests in Detecting SARS-CoV-2 Infection: a Meta-Analysis," Diagnostics. 10(5), May 19, 2020, pp. 1-15.
Luca Perico, et al., "COVID-19 and lombardy: TESTing the impact of the first wave of the pandemic," EBioMedicine. 61 (2020) 103069, pp. 1-7.
Zhengtu Li, et al., "Development and clinical application of a rapid IgM-IgG combined antibody test for SARS-CoV-2 infection diagnosis," Journal of Medical Virology 2020; 92, pp. 1518-1524.
Maia Norman, et al., "Ultra-Sensitive High-Resolution Profiling of Anti-SARS-CoV-2 Antibodies for Detecting Early Seroconversion in COVID-19 Patients," medRxiv, May 2, 2020, XP055769481, DOI: 10.1101/2020.04.28.20083691.
Emily Adams, et al., "Antibody testing for COVID-19: a report from the National COVID Scientific Advisory Panel," medRxi v, Jul. 7, 2020, pp. 1-21, XP055856254, DOI: 10.1101/2020.04.15.20066407.
Kevin Ng, et al., "Pre-existing and de novo humoral immunity to SARS-CoV-2 in humans," bioRxiv, May 15, 2020, XP055785007, DOI: 10.1101/2020.05.14.095414.
Davide F. Robbiani, et al., "Convergent antibody responses to SARS-CoV-2 in convalescent individuals," Nature, vol. 584, Aug. 20, 2020, pp. 437-442.
Christoph Kreer, et al., "Longitudinal Isolation of Potent Near-Germline SARS-CoV-2-Neutralizing Antibodies from COVID-19 Patients," 2020, Cell 182, pp. 843-854.
Dmitriy V. Sotnikov, et al., "Theoretical and Experimental Comparison of Different Formats of Immunochromatographic Serodiagnostics," Sensors 2018, 18, 36; doi:10.3390/s18010036, pp. 1-15.
Rachael C. Abbott, et al., "A Rapid Field Test for Sylvatic Plague Exposure in Wild Animals," Journal of Wildlife Diseases, 50(2), 2014, pp. 000-000.
M. Manasa, et al., "Protein-G-based lateral flow assay for rapid serodiagnosis of brucellosis in domesticated animals," Journal of Immunoassay and Immunochemistry, 2019, vol. 40, No. 2, pp. 149-158.
Philippe Thullier, et al., "Short Report: Serodiagnosis of Plague in Humans and Rats Using a Rapid Test," The American Journal of Tropical Medicine and Hygiene, 69(4), 2003, pp. 450-451.
Nadin Younes, et al., "Challenges in Laboratory Diagnosis of the Novel Coronavirus SARS-CoV-2," Viruses 2020, 12, 582, pp. 1-27.
Shuai Xia, et al., "Fusion mechanism of 2019-nCOV and fusion inhibitors targeting HR1 domain in spike protein," Cellular & Molecular Immunology (2020) 17:765-767.
Daniel Wrapp et al., "Cryo-EM structure of the 2019-nCoV spike in the prefusion conformation," Science 10.1126/science.abb2507 (2020).
Daniel Wrapp, et al., Supplementary Materials for "Cryo-EM structure of the 2019-nCoV spike in the prefusion conformation," published Feb. 19, 2020 on Science First Release DOI: 10.1126/science.abb2507, pp. 1-19.

* cited by examiner

QCVNLTTRTQLPPAYTNSFTRGVYYPDKVFRSSVLHSTQDLFLPFFSNVTWFHAIHVSGTNGTKRFDNPVLPFNDGV
YFASTEKSNIIRGWIFGTTLDSKTQSLLIVNNATNVVIKVCEFQFCNDPFLGVYYHKNNKSWMESEFRVYSSANNCT
FEYVSQPFLMDLEGKQGNFKNLREFVFKNIDGYFKIYSKHTPINLVRDLPQGFSALEPLVDLPIGINITRFQTLLAL
HRSYLTPGDSSSGWTAGAAAYYVGYLQPRTFLLKYNENGTITDAVDCALDPLSETKCTLKSFTVEKGIYQTSNFRVQ
PTESIVRFPNITNLCPFGEVFNATRFASVYAWNRKRISNCVADYSVLYNSASFSTFKCYGVSPTKLNDLCFTNVYAD
SFVIRGDEVRQIAPGQTGKIADYNYKLPDDFTGCVIAWNSNNLDSKVGGNYNYLYRLFRKSNLKPFERDISTEIYQA
GSTPCNGVEGFNCYFPLQSYGFQPTNGVGYQPYRVVVLSFELLHAPATVCGPKKSTNLVKNKCVNFNFNGLTGTGVL
TESNKKFLPFQQFGRDIADTTDAVRDPQTLEILDITPCSFGGVSVITPGTNTSNQVAVLYQDVNCTEVPVAIHADQL
TPTWRVYSTGSNVFQTRAGCLIGAEHVNNSYECDIPIGAGICASYQTQTNSPGSASSVASQSIIAYTMSLGAENSVA
YSNNSIAIPTNFTISVTTEILPVSMTKTSVDCTMYICGDSTECSNLLLQYGSFCTQLNRALTGIAVEQDKNTQEVFA
QVKQIYKTPPIKDFGGFNFSQILPDPSKPSKRSFIEDLLFNKVTLADAGFIKQYGDCLGDIAARDLICAQKFNGLTV
LPPLLTDEMIAQYTSALLAGTITSGWTFGAGAALQIPFAMQMAYRFNGIGVTQNVLYENQKLIANQFNSAIGKIQDS
LSSTASALGKLQDVVNQNAQALNTLVKQLSSNFGAISSVLNDILSRLDPPEAEVQIDRLITGRLQSLQTYVTQQLIR
AAEIRASANLAATKMSECVLGQSKRVDFCGKGYHLMSFPQSAPHGVVFLHVTYVPAQEKNFTTAPAICHDGKAHFPR
EGVFVSNGTHWFVTQRNFYEPQIITTDNTFVSGNCDVVIGIVNNTVYDPLQPELDSFKEELDKYFKNHTSPDVDLGD
ISGINASVVNIQKEIDRLNEVAKNLNESLIDLQELGKYEQGYIPEAPRDGQAYVRKDGEWVLLSTFLGHHHHHH

FIG. 4

SEQUENCE LISTING

<160> NUMBER OF SEQ ID NOS: 5

<210> SEQ ID NO 1
<211> LENGTH: 1273
<212> TYPE: PRT
<213> ORGANISM: severe acute respiratory syndrome coronavirus 2

<400> SEQUENCE: 1

-continued

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
```

-continued

```
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845
```

-continued

```
Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                 1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245
```

-continued

```
Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 2
<211> LENGTH: 27
<212> TYPE: PRT
<213> ORGANISM: Artificial Sequence
<220> FEATURE:
<223> OTHER INFORMATION: C-terminal T4 fibritin foldon motif

<400> SEQUENCE: 2

Gly Tyr Ile Pro Glu Ala Pro Arg Gly Asp Gln Ala Tyr Val Arg Lys
1               5                   10                  15

Asp Gly Glu Trp Val Leu Leu Ser Thr Phe Leu
            20                  25


<210> SEQ ID NO 3
<211> LENGTH: 1229
<212> TYPE: PRT
<213> ORGANISM: Artificial Sequence
<220> FEATURE:
<223> OTHER INFORMATION: Recombinant SARS-CoV-2 spike protein antigen

<400> SEQUENCE: 3

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255
```

-continued

```
Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gly Ser Ala Ser
            660                 665                 670
```

-continued

```
Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
```

-continued

```
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Gly Tyr Ile Pro Glu  Ala Pro Arg
    1190                1195                1200

Asp Gly  Gln Ala Tyr Val Arg  Lys Asp Gly Glu Trp  Val Leu Leu
    1205                1210                1215

Ser Thr  Phe Leu Gly His His  His His His His
    1220                1225


<210> SEQ ID NO 4
<211> LENGTH: 7
<212> TYPE: PRT
<213> ORGANISM: Artificial Sequence
<220> FEATURE:
<223> OTHER INFORMATION: polyhistidine tag

<400> SEQUENCE: 4

Gly His His His His His His
1               5


<210> SEQ ID NO 5
<211> LENGTH: 4
<212> TYPE: PRT
<213> ORGANISM: Artificial Sequence
<220> FEATURE:
<223> OTHER INFORMATION: furin cleavage site

<400> SEQUENCE: 5

Gly Ser Ala Ser
1
```

LATERAL FLOW DEVICE FOR DETECTING SARS-CoV-2 ANTIBODIES IN HUMAN AND ANIMAL SAMPLES

CROSS-REFERENCE TO RELATED APPLICATIONS

This application claims the benefit of U.S. Provisional Application No. 63/064,225, filed Aug. 11, 2020, the entire contents of which are incorporated herein by reference in their entirety.

FIELD OF THE INVENTION

The invention relates to a device for the detection of antibodies to SARS-CoV-2 in a human or animal sample of bodily fluid, such as whole blood, serum, or plasma. In particular, the invention relates to a rapid point-of-care lateral flow SARS-CoV-2 antibody test that is suitable for testing both human and animal samples.

BACKGROUND

Coronaviruses are a large family of viruses that can cause illnesses ranging widely in severity. The first known severe illness caused by a coronavirus emerged with the 2003 Severe Acute Respiratory Syndrome (SARS) epidemic in China. A second outbreak of severe illness began in 2012 in Saudi Arabia with the Middle East Respiratory Syndrome (MERS).

On Dec. 31, 2019, Chinese authorities alerted the World Health Organization of an outbreak of a novel strain of coronavirus causing severe illness, which was subsequently named SARS-CoV-2. SARS-CoV-2 is the virus that causes the disease referred to as COVID-19. As of Aug. 10, 2020, approximately 19.7 million COVID-19 cases have been documented worldwide, although many more mild cases have likely gone undiagnosed. The virus has killed over 728,000 people.

Shortly after the epidemic began, Chinese scientists sequenced the genome of SARS-CoV-2 and made the data available to researchers worldwide. The number of COVID-19 cases have been increasing because of human to human transmission after a single introduction into the human population.

SARS-CoV-2 spike proteins are located on the outside of the virus. The virus uses its spike protein to grab and penetrate the outer walls of human and animal cells. Scientists have focused on two distinctive features of SARS-CoV-2's spike protein—the Receptor Binding Domain (RBD) portion that binds to cells and the cleavage site that opens the virus up and allows it to enter host cells. The S1 and S2 subunits of the spike protein are responsible for receptor recognition and membrane fusion, respectively.

Scientists are still learning about this virus, but it appears that it can spread from people to animals in some situations, especially after close contact with a person sick with COVID-19. Based on information available on the website of the Centers for Disease Control and Prevention (CDC), we know that cats, dogs, and a few other types of animals can be infected with SARS-CoV-2, but we do not yet know all of the animals that can get infected. There have been reports of animals being infected with the virus worldwide.

A small number of pet cats and dogs have been reported to be infected with the virus in several countries, including the United States. Most of these pets became sick after contact with people with COVID-19. Several lions and tigers at a New York zoo tested positive for SARS-CoV-2 after showing signs of respiratory illness. Public health officials believe these large cats became sick after being exposed to a zoo employee who was infected with SARS-CoV-2.

SARS-CoV-2 was recently discovered in mink (which are closely related to ferrets) on multiple farms in the Netherlands. The mink showed respiratory and gastrointestinal signs; the farms also experienced an increase in mink deaths. Because some workers on these farms had symptoms of COVID-19, it is likely that infected farm workers were the source of the mink infections. Some farm cats on several mink farms also developed antibodies to this virus, suggesting they had been exposed to the virus at some point.

The CDC, U.S. Department of Agriculture (USDA), and state public health and animal health officials are working in some states to conduct active surveillance of SARS-CoV-2 in pets, including cats, dogs, and other small mammals, that had contact with a person with COVID-19. These animals are being tested for SARS-CoV-2 infection, as well as tested to see whether the pet develops antibodies to this virus. This work is being done to help us better understand how common SARS-CoV-2 infection might be in pets as well as the possible role of pets in the spread of this virus. The USDA maintains a list of cases of SAR-CoV-2 (the same virus that causes COVID-19 in humans) in animals in the United States that have been confirmed by the USDA's National Veterinary Services Laboratories.

Research on SARS-Cov-2 in animals is limited, but studies are underway to learn more about how this virus can affect different animals. Recent research shows that ferrets, cats, and golden Syrian hamsters can be experimentally infected with the virus and can spread the infection to other animals of the same species in laboratory settings. A number of studies have investigated non-human primates as models for human infection. Rhesus macaques, cynomolgus macaques, Grivets, and common marmosets can become infected SARS-CoV-2 and become sick in a laboratory setting. Mice, pigs, chickens, and ducks do not seem to become infected or spread the infection based on results from these studies. Data from one study suggest some dogs can get infected but might not spread the virus to other dogs as easily compared to cats and ferrets, which can easily spread the virus to other animals of the same species. These findings were based on a small number of animals, and do not show whether animals can spread infection to people. More studies are needed to understand if and how different animals could be affected by COVID-19.

It is important to investigate the connections between the health of people and animals. Considering that humans and at least some animal species can be infected with SARS-CoV-2, it would be of benefit to provide a diagnostic antibody test kit that can suitably detect antibodies to the virus in samples from both humans and animals. Presently, available test kits employ secondary antibodies that are specific for immunoglobulins from either humans or particular animal species. This requires that separate tests be used for humans and animal, which is not convenient.

It would be particularly desirable to provide a lateral flow antibody test. Lateral flow (LF) tests are membrane-based immunoassay tests. LF devices have a test strip consisting of a membrane, such as porous paper or a sintered polymer, which enables capillary flow of a sample and detection reagents. The membrane also holds substances that form test and control lines. One end of the membrane is fitted with a sample pad that contacts another pad used to store the detection conjugate. The other end of the membrane has a wicking pad that holds fluids and reagents that have migrated via capillary action through the membrane. LF devices exist for a wide range of targets including the detection of infectious agents, metabolic molecules, antibodies, toxins and drugs for use in human and veterinary applications.

LF tests are typically modelled on existing immunoassay formats and can be sandwich assays or competitive assays. Many assay variations are possible, but a positive signal is usually achieved by the specific accumulation of a detection complex at the test line.

LF devices usually need to be specifically developed in an iterative process for the desired application. Each component of the test strip of a LF device requires specific evaluation followed by testing to determine the optimal combination of components. The identification of the most suitable membrane is an important step in the test strip development as this determines the capillary flow properties that need to be compatible with the type of sample to be tested. Also, samples may need to be pre-treated in order to achieve the required capillary flow properties. For instance, viscous or highly concentrated samples, such as serum, may need to be diluted in a suitable buffer, and/or cells and aggregates may need to be removed from the sample. Additional treatments such as the adjustment of pH or salt concentrations that enhance antibody/ligand binding may also be required for optimal performance of the test.

A rapid point-of-care lateral flow SARS-CoV-2 antibody test that would be suitable for testing both human and animal samples would be advantageous because informed treatment and management decisions could be made immediately after detection of the SARS-CoV-2 antibodies. Antibody tests are also helpful in confirming results of antigen-detection tests. This could help prevent the spread from human to human, or from people to animals in some situations, as well as limit the spread of the infection from animals to other animals of the same species. It is at least important to potentially limit the spread of the virus to a single facility, home or location, and a reliable lateral flow SARS-CoV-2 antibody test that can be used for human as well as animal samples would be useful in this regard.

SUMMARY OF THE INVENTION

In one aspect, the present invention provides a lateral flow device for the detection of antibodies to severe acute respiratory syndrome coronavirus 2 (SARS-CoV-2) in a sample of bodily fluid of an animal or human. This device includes: a) a strip formed of a material enabling capillary flow of fluid along a portion of the strip; b) a sample pad located proximal to one end of the strip for receiving the sample of the bodily fluid, c) a conjugate pad located in the strip so that in operation the sample flows under capillary action through the strip from the sample pad to the conjugate pad and mobilizes a conjugate contained in the conjugate pad, the conjugate comprising a recombinant SARS-CoV-2 spike protein antigen that has been conjugated to a detection agent; and d) a detection band comprising an Fc-binding protein immobilized within the strip along a band located substantially perpendicular to the direction of flow of the sample along the strip so that when the mobilized spike protein conjugate in the sample contacts the Fc-binding protein in the detection band the presence of the antibodies to the SARS-CoV-2 virus in the sample is indicated by a visible color change. In one embodiment, the device further includes a wicking pad for receiving and retaining sample after passing through the detection band.

If anti-SARS-CoV-2 antibodies are present in the sample, a formed complex comprising the mobilized spike protein conjugate and the anti-SARS-CoV-2 antibodies in the sample contacts the immobilized Fc-binding protein in the detection band such that the presence of the antibodies to SARS-CoV-2 is indicated with a visual signal. If anti-SARS-CoV-2 antibodies are not present in the sample, the conjugate is not immobilized at the detection band and continues to migrate to the wicking pad. The lack of formation of a visual signal at the detection band indicates the sample is negative for antibodies to SARS-CoV-2.

In one embodiment, the Fc-binding protein in the detection band of the device is Protein G, Protein A, or a Protein A/G fusion protein. In one specific embodiment, the FC-binding protein is Protein A or Protein G.

In some embodiments of the device, the detection agent conjugated to the SARS-CoV-2 spike protein antigen on the conjugate pad is selected from metallic nanoparticles or nanoshells, non-metallic nanoparticles or nanoshells, enzymes, or fluorescent molecules. In one specific embodiment, the detection agent includes nanoparticles or nanoshells of metallic gold.

In one embodiment of the device, the recombinant spike protein antigen present in the conjugate is in a prefusion conformation. In one particular embodiment of the device, the recombinant spike protein antigen comprises a fragment of a wild-type 2019-nCoVS protein having the amino acid sequence of SEQ ID NO: 1, wherein the fragment comprises the S1 and S2 domains and includes a double proline substitution at positions 986 and 987 of the wild-type protein. In one embodiment, the fragment of the wild-type 2019-nCoVS protein comprising the S1 and S2 domains and the double proline substitution corresponds to residues 14 to 1208 of the wild-type 2019-nCoVS protein. In another embodiment, the fragment of the wild-type 2019-nCoVS protein comprising the S1 and S2 domains and the double proline substitution further includes a furin cleavage site "GSAS" (SEQ ID NO: 5) at positions 682 to 685 of the wild-type protein. In yet another embodiment, the fragment of the wild-type 2019-nCoVS protein including the S1 and S2 domains, the double proline substitution, and the furin cleavage site further comprises a C-terminal T4 fibritin foldon motif "GYIPEAPRGDQAYVRKDGEWVLLSTFL" (SEQ ID NO: 2).

In some embodiments, the sample pad includes a filter membrane for removing one or more components from the sample. In one embodiment, the one or more components removed from the sample by the filter membrane of the sample pad are cells, cellular material, fats, or particulate matter.

In one embodiment, the device further includes a control line located substantially perpendicular to the direction of flow of the sample along the strip. In one embodiment, deposited on the control line is an antibody capable of capturing any excess mobilized spike protein conjugate as it crosses the control line, said binding at the control line being indicated by a visible color change. In one embodiment, the antibody capable of capturing any excess spike protein conjugate is a monoclonal antibody which specifically binds the spike protein antigen in the spike protein conjugate.

In another embodiment, the conjugate pad further comprises an immunoglobulin conjugated to a detection agent so that in operation the sample flows from the sample pad to the conjugate pad and mobilizes the immunoglobulin conjugate which passes over the detection band without reactivity and crosses the control line. In this embodiment, deposited at the control line is an antibody capable of binding to the mobilized immunoglobulin conjugate as it crosses the control line, said binding at the control line being indicated by a visible color change. In one embodiment, the immunoglobulin in the immunoglobulin conjugate is from animal species other than the species from which the sample of bodily fluid is derived. In one embodiment, the detection agent conjugated to the immunoglobulin in the immunoglobulin conjugate is selected from metallic nanoparticles or nanoshells, non-metallic nanoparticles or nanoshells, enzymes, or fluorescent molecules. In one specific embodiment, the detection agent conjugated to the immunoglobulin in the immunoglobulin conjugate comprises nanoparticles or nanoshells of metallic gold.

In one embodiment of the device, the strip is formed of nitrocellulose. This can pertain to any of the embodiments of the device described above.

In one embodiment, the sample of bodily fluid which is to be received by the sample pad is from an animal selected from a canine, a feline, equine, caprine, ovine, murine, avian, bovine, or a mustelid animal. In another embodiment, the sample of bodily fluid which is to be received by the sample pad is from a human. In one embodiment, the bodily fluid is selected from whole blood, blood serum, blood plasma, mucous, saliva, and urine.

The present invention further provides a method for the detection of antibodies to severe acute respiratory syndrome coronavirus 2 (SARS-CoV-2) in a bodily fluid of an animal or human. This method includes using a device according to any of the embodiments described above.

The present invention further provides a method for the detection of antibodies to severe acute respiratory syndrome coronavirus 2 (SARS-CoV-2) in a sample of bodily fluid of an animal or human. This method includes contacting the sample with a conjugate comprising a recombinant SARS-CoV-2 spike protein antigen that has been conjugated to a detection agent, wherein an antigen-antibody complex is formed between the SARS-CoV-2 spike protein antigen conjugate and SARS-CoV-2 antibodies present in the sample; capturing the formed antigen-antibody complex with an Fc-binding molecule; and detecting the captured complex. In one embodiment of the method, the Fc-binding protein used to capture the formed antigen-antibody complex is Protein G, Protein A, or a Protein A/G fusion protein.

In one embodiment of the method, the detection agent conjugated to the SARS-CoV-2 spike protein antigen is selected from metallic nanoparticles or nanoshells, non-metallic nanoparticles or nanoshells, enzymes, and fluorescent molecules. In one specific embodiment of the method, the detection agent comprises nanoparticles or nanoshells of metallic gold.

In some embodiments of the methods, the recombinant spike protein antigen that has been conjugated to the detection agent is in a prefusion conformation. In one embodiment, the recombinant spike protein antigen comprises a fragment of a wild-type 2019-nCoVS protein having the amino acid sequence of SEQ ID NO: 1, wherein the fragment comprises the S1 and S2 domains and includes a double proline substitution at positions 986 and 987 of the wild-type protein. In one embodiment of the method, the fragment comprising the S1 and S2 domains and the double proline substitution corresponds to residues 14 to 1208 of the wild-type 2019-nCoVS protein. In another embodiment of the method, the fragment of the wild-type 2019-nCoVS protein comprising the S1 and S2 domains and the double proline substitution further comprises a furin cleavage site "GSAS" (SEQ ID NO: 5) at positions 682 to 685 of the wild-type protein. In yet another embodiment of the method, the fragment of the wild-type 2019-nCoVS protein which includes the S1 and S2 domains, the double proline substitution, and the furin cleavage site further comprises a C-terminal T4 fibritin foldon motif "GYIPEAPRGDQAYVRKDGEWVLLSTFL" (SEQ ID NO: 2).

BRIEF DESCRIPTION OF THE DRAWINGS

FIG. 4 is a representation of one embodiment of a recombinant SARS-CoV-2 spike protein antigen corresponding to SEQ ID NO: 3 that can be employed in the device and methods of the present invention. The furin cleavage site knockout "GSAS" (SEQ ID NO: 5) and the double proline substitution "PP" are each underlined and in bold print. The C-terminal T4 Fibritin trimerization motif (SEQ ID NO: 2) is shown with dashed underlining and the 6× polyhistidine tag (SEQ ID NO: 4) is double-underlined.

Figure 1:
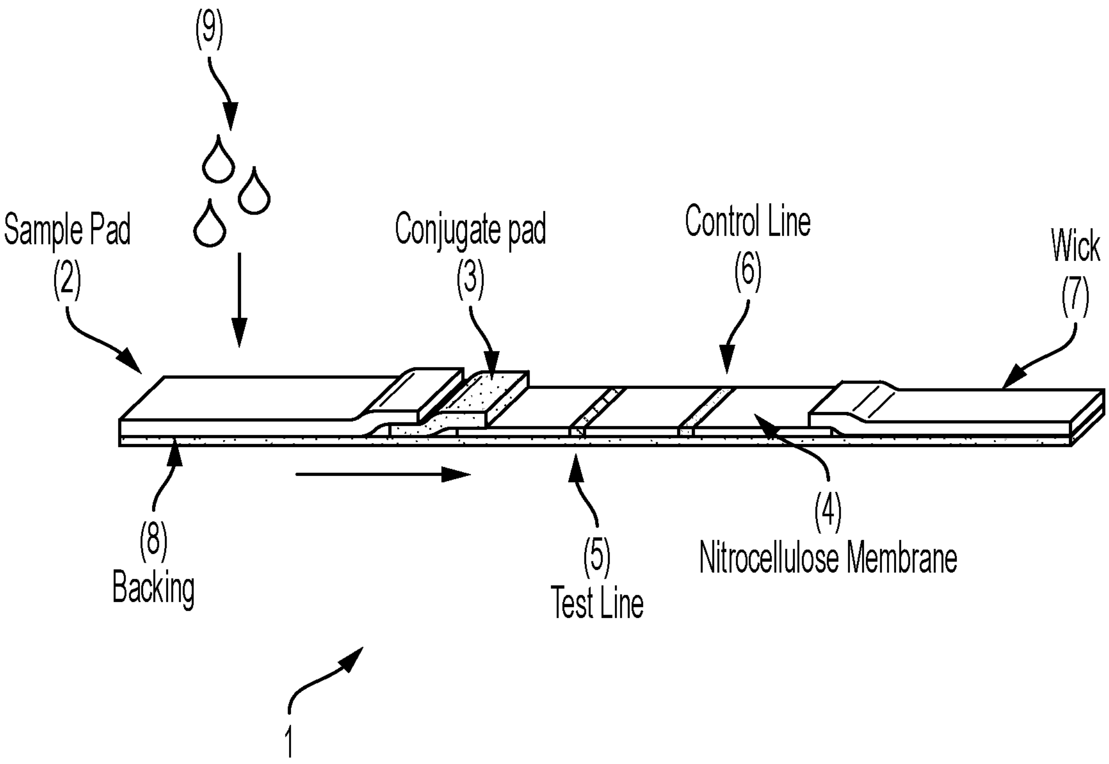
FIG. 1 is a schematic representation of a LF device of the invention.

Other objects, aspects, features and advantages of the present invention will become apparent from the following description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Definitions

Throughout this specification, unless the context requires otherwise, the words "comprise," "comprises," and "comprising" will be understood to imply the inclusion of a stated step or element or group of steps or elements but not the exclusion of any other step or element or group of steps or elements.

The terms "protein", "protein fragment", "polypeptide", and "peptide" may be used interchangeably herein to refer to a polymer of amino acid residues and to variants and synthetic and naturally occurring analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers and naturally occurring chemical derivatives thereof.

The term "antibody", also referred to as "immunoglobulin", is a Y-shaped protein of the immune system that specifically identifies foreign objects or antigens, such as the components of bacteria, yeasts, parasites, and viruses. Each tip of the 'Y' of an antibody contains an antigen-binding site that is specific for a particular epitope on an antigen, allowing these two structures to bind together with precision. The production of a given antibody is increased upon exposure to an antigen (e.g., a microbial or viral antigen) that specifically interacts with that antibody. Hence, the detection of antigen-specific antibodies in a sample from a subject can inform whether that subject is currently exposed to, or has been previously exposed to, a given microbe, such as a virus, bacteria, fungus, or parasite. An "antibody" typically comprises all or a portion of an Fc region, to facilitate detection by an Fc-binding protein, and may also comprise one or more antigen-binding sites, to facilitate detection by an antibody-specific binding agent, such as an antigen or antigenic peptide. The antibodies can be, e.g., of IgG, IgE, IgD, IgM, or IgA type.

The term "antigen" means a molecule having distinct surface features or epitopes capable of stimulating a specific immune response. Antibodies (immunoglobulins) are produced by the immune system in response to exposure to antigens. Antigens maybe proteins, carbohydrates or lipids, although only protein antigens are classified as immunogens because carbohydrates and lipids cannot elicit an immune response on their own.

An "antigen-binding site," or "binding portion" of an antibody, refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". In an antibody molecule, the three hypervariable regions of a light chain and the three hypervariable regions of a heavy chain are disposed relative to each other in three dimensional space to form an antigen-binding surface. The antigen-binding surface is complementary to the three dimensional surface of a bound antigen, and the three hypervariable regions of each of the heavy and light chains are referred to as "complementarity-determining regions," or "CDRs."

The term "Fc-binding protein" refers to a protein or polypeptide capable of binding to the fragment crystallizable region (Fc region) of an antibody. The Fc region is the tail region of an antibody that interacts with cell surface Fc receptors and certain proteins of the complement system. In IgG, IgA and IgD antibody isotypes, the Fc region is composed of two identical protein fragments, derived from the second and third constant domains of the antibody's two heavy chains. IgM and IgE Fc regions contain three heavy chain constant domains (CH domains 2-4) in each polypeptide chain. The Fc regions of IgG antibodies bears a highly conserved N-glycosylation site. The N-glycans attached to this site are predominantly core-fucosylated diantennary structures of the complex type. In addition, small amounts of these N-glycans also bear bisecting GlcNAc and. alpha-2,6 linked sialic acid residues. The Fab region of an antibody contains variable sections that define the target-specificity of the antibody, and in contrast, the Fc region of all antibodies in a class are the same for each species; they are constant rather than variable.

The term "nanoparticles" means uniform particles having a size of 1-200 nm.

The term "nanoshells" means nanoparticles that consist of a core and a metallic shell (usually gold).

Lateral Flow Device and Kits

With reference to the figures, FIG. 1 shows a LF device (1) of the invention. The device (1) has a sample pad (2) that makes a sample of bodily fluid from an animal or human amenable to capillary flow, a conjugate pad (3) including a mobilizable conjugate comprising a recombinant SARS-CoV-2 spike protein antigen that has been conjugated to a detection agent, a membrane (4), and a wicking pad (7) for receiving and holding fluid that has travelled by capillary flow from the sample pad (2) and through the conjugate pad (3) and the membrane (4). A detection band/test line (5) is shown which comprises an immobilized Fc-binding protein. Band (6) is a positive control band. The device (1) can further include a backing (8).

When a fluid sample (9) is deposited on the sample pad (2), or the sample pad (2) is dipped into the fluid sample, fluid travels from the sample pad (2) by capillary flow to the conjugate pad (3) where it comes into contact with a recombinant SARS-CoV-2 spike protein antigen that has been conjugated to a detection agent (not shown). Specific antibodies in the sample will react with the SARS-CoV-2 spike protein conjugate on conjugate pad (3). The fluid mobilizes the conjugate in the sample and transports it to the detection band/test line (5). Specifically, the antibody-spike protein-detection agent complex formed between any antibodies in the sample and the SARS-CoV-2 spike protein conjugate at conjugate pad (3) migrates across membrane (4) to the detection band/test line (5) where the complexed antibody is immobilized by the Fc-binding protein deposited there. The accumulation of the detection agent on the detection band/test line (5) forms a visual signal, i.e., a color change if antibodies are present, indicating a positive result. If anti-SARS-CoV-2 antibodies are not present in the sample, the conjugate is not immobilized at the detection band (5) and continues to migrate to the wicking pad (7). The lack of formation of a visual signal at the detection band (5) indicates the sample is negative for antibodies to SARS-CoV-2.

Figure 2:
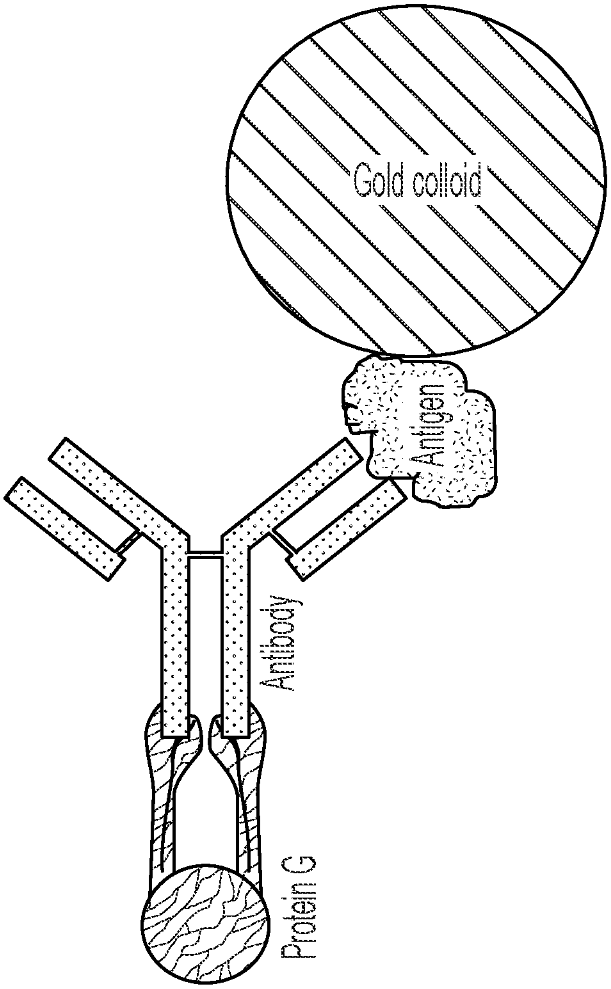
FIG. 2 is a schematic representation of one embodiment of the device and method of the invention wherein an anti-SARS-Cov-2-antibody-spike protein-gold complex is immobilized by an Fc-binding protein (e.g., Protein G or Protein A). In operation, the immobilization by the Fc-binding protein occurs at the test line of the LF device and forms a visual signal.

Shown (schematically) in FIG. 2 is one embodiment of the complex which is captured at the detection band (5) of LF device (1) in FIG. 1 when antibodies to the SARS-CoV-2 virus are present in the sample. In the embodiment shown in FIG. 2, the detection agent is represented as a gold colloid (gold nanoparticle). The depicted complex is formed when the antibody-spike protein-gold complex migrates across the membrane where the complexed antibody from the sample is immobilized by the Fc-binding protein on the detection band.

Referring again to LF device (1) in FIG. 1, in one embodiment, deposited at control band (6) is an antibody (not shown) which is capable of capturing any excess mobilized spike protein conjugate as it crosses the control line under the continued influence of capillary flow, wherein this binding at the control line is indicated by a visible color change. In one embodiment, the antibody capable of capturing excess spike protein conjugate is a monoclonal antibody which specifically binds the spike protein in the SARS-CoV-2 spike protein conjugate.

In another embodiment of device (1) in FIG. 1, the conjugate pad (3) further includes an immunoglobulin conjugated to a detection agent (not shown) so that in operation the sample (9) flows from sample pad (2) to conjugate pad (3) and mobilizes the immunoglobulin conjugate which passes over detection band/test line (5) without reactivity and crosses the control line (6). In one embodiment, deposited at the control line (6) is an antibody capable of binding to the mobilized immunoglobulin conjugate as it crosses control line (6), the binding at control line (6) being indicated by a visible color change. In one embodiment, the immunoglobulin in the immunoglobulin conjugate is from an animal species other than the species from which the sample (9) of bodily fluid is derived.

Figure 3:
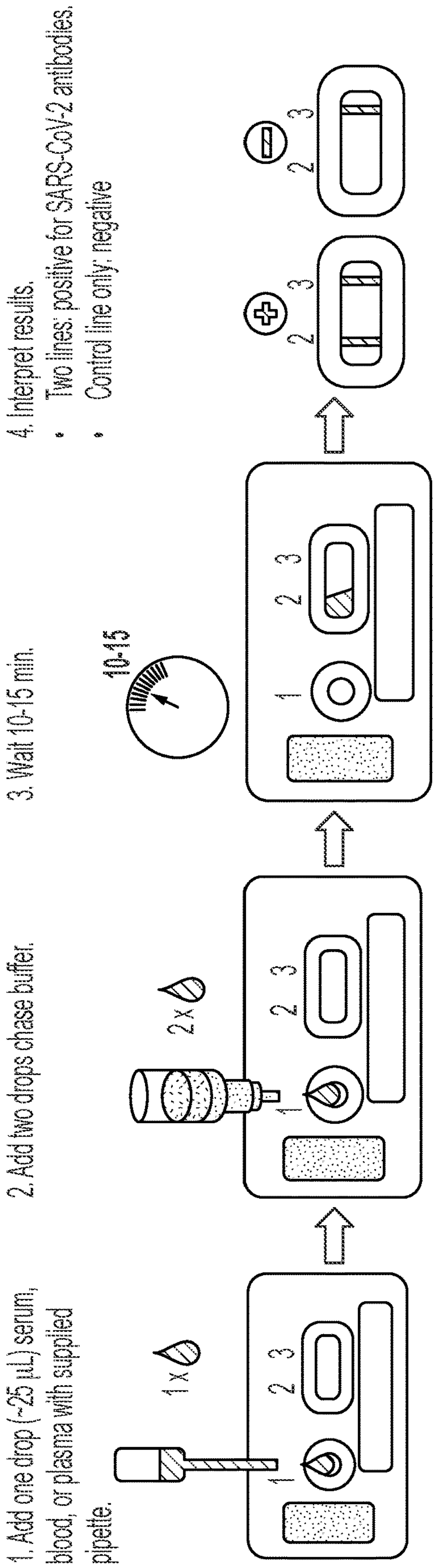
FIG. 3 is a schematic representation of one embodiment of the test instructions for the SARS-CoV-2 antibody lateral flow test.

Also included are kits comprising one or more of the LF devices and instructions for using the device to detect an antibody in a test sample. FIG. 3 is schematic representation of one embodiment of the test instructions for the SARS-CoV-2 antibody lateral flow test.

The lateral flow device of the invention detects antibodies to SARS-CoV-2 in a bodily fluid of an animal or human. In one aspect, the device comprises: a) a strip formed of a material enabling capillary flow of fluid along a portion of the strip; b) a sample pad located proximal to one end of the strip for receiving the sample of the bodily fluid, c) a conjugate pad located in the strip so that in operation the sample flows under capillary action through the strip from the sample pad to the conjugate pad and mobilizes a conjugate contained in the conjugate pad, the conjugate comprising a recombinant SARS-CoV-2 spike protein antigen that has been conjugated to a detection agent; d) a detection band comprising an Fc-binding protein immobilized within the strip along a band located substantially perpendicular to the direction of flow of the sample along the strip so that when the mobilized spike protein conjugate in the sample contacts the Fc-binding protein in the detection band the presence of the antibodies to the SARS-CoV-2 virus in the sample is indicated by a visible color change; e) a control line located substantially perpendicular to the direction of flow of the sample along the strip, the control region being in fluid communication with the sample when it is loaded to the sample loading region; and f) a wicking pad for receiving and retaining the sample after passing through the detection band.

Suitable methods for immobilizing capture entities such as the spike protein antigen on solid phases include ionic, hydrophobic, covalent interactions and the like. In terms of immobilizing the conjugates on the conjugate pad, they are typically sprayed onto the conjugate pad with a specialized sprayer similar to an airbrush. The reagent dries on the conjugate pad. Likewise, the test/detection band and control line are striped onto the test strip (e.g., nitrocellulose) with a precision dispensing machine. The proteins bind to the nitrocellulose and are immobilized this way.

The sample pad not only receives sample fluid for testing, but removes components from the fluid that might otherwise impede capillary flow of the fluid through the strip or adversely affect detection of the antibodies at the detection band. The components that may be removed by the sample pad include cells, cellular material, fats, and particulate matter. For the purpose of detecting antibodies to SARS-CoV-2 in a blood sample from an animal or human, the sample pad serves as a blood filtering pad that removes blood components, such as red blood cells from whole blood that might otherwise interfere with the flow of the sample along the strip. The sample pad avoids any requirement for pre-treatment of the sample.

Nitrocellulose was found to be a suitable material from which the strip is made. Other materials may also be suitable provided they allow the desired capillary flow rate and enable suitable detection sensitivity, such as a PVDF membrane, polyethylene membrane, nylon membrane, or a similar type of membrane.

As will be appreciated, any bodily fluid that contains or is suspected to contain antibodies to SARS-CoV2 may be used as the fluid sample for testing using the device of the invention. Such fluids can include whole blood, blood serum, blood plasma, milk, mucous, saliva, sputum, semen, sweat and urine. In one embodiment, the fluid is whole blood, blood plasma, or blood serum.

In one embodiment, the sample of bodily fluid is from an animal selected from a canine, a feline, equine, caprine, murine, avian, ovine, bovine, or a mustelid animal. In another embodiment, the sample of bodily fluid is from a human.

The detection agent is any agent that provides a. detectable change when accumulated at the test line or control line. Accumulation of the detection agent at the test line indicates that antibodies are present in the fluid sample. In practice, the detection agent is conjugated directly or indirectly to a recombinant SARS-CoV2 spike protein to form a conjugate contained in the conjugate pad that is capable of binding to a SARS-CoV2 antibody from the sample. In some embodiments, the conjugate pad can further include an immunoglobulin which is conjugated directly or indirectly to a detection agent so that in operation, the sample mobilizes the immunoglobulin conjugate which passes over the detection band without reactivity and crosses a control line on which is deposited an antibody capable of binding to the immunoglobulin present in the mobilized immunoglobulin conjugate. As the immunoglobulin conjugate crosses the control line and the antibody deposited at the control line binds to it, the binding is indicated by a visible color change.

The accumulation of the detection agent causes a visible color change or observable fluorescence, or any other suitable change at the test line/detection band and control line. In various specifically contemplated embodiments of the invention, the detection agent conjugated to the SARS-CoV-2 spike protein antigen on the conjugate pad is selected from metallic nanoparticles or nanoshells, non-metallic nanoparticles or nanoshells, enzymes, or fluorescent molecules. In specific embodiments, the metallic nanoparticle or metallic nanoshell conjugated to the spike protein antigen is selected from gold particles, silver particles, copper particles, platinum particles, cadmium particles, composite particles, gold hollow spheres, gold-coated silica nanoshells, or silica-coated gold shells. In one desired embodiment, the detection agent conjugated to the spike protein antigen includes nanoparticles or nanoshells of metallic gold. In other specifically contemplated embodiments of the invention, the detection agent conjugated to the immunoglobulin on the conjugate pad is selected from metallic nanoparticles or nanoshells, non-metallic nanoparticles or nanoshells, enzymes, or fluorescent molecules. In specific embodiments, the metallic nanoparticle or metallic nanoshell conjugated to the immunoglobulin is selected from gold particles, silver particles, copper particles, platinum particles, cadmium particles, composite particles, gold hollow spheres, gold-coated silica nanoshells, and silica-coated gold shells. In one embodiment, it is contemplated that the detection agent conjugated to the spike protein antigen on the conjugate pad may be the same or different from the detection agent conjugated to the immunoglobulin on the conjugate pad. In one desired embodiment, the detection agent conjugated to the spike protein antigen and the detection agent conjugated to the immunoglobulin are both gold nanoparticles, to create colloidal gold conjugates.

The detection band of the strip comprises an Fc-binding protein immobilized within the strip. Specific examples of Fc-binding molecules include Protein A, Protein G, Protein A/G fusion proteins, Protein L, and fragments and variants thereof which retain the ability to specifically bind to the Fc region of an antibody.

Protein A is a 40-60 kDa MSCRAMM (microbial surface components recognizing adhesive matrix molecules) surface protein found in the cell wall of *Staphylococcus aureus*, and is encoded by the spa gene. Wild-type Protein A is composed of five homologous Ig-binding domains that fold into a three-helix bundle, and which can individually bind to the Fc regions of an antibody. Protein A binds with high affinity to human IgG1 and IgG2 and with moderate affinity to human IgM, IgA and IgE.

Protein G is an immunoglobulin-binding protein expressed in group C and G Streptococcal bacteria (see, e.g., Sjobring et al., J Biol Chem. 266:399-405, 1991). The NMR solution structure (see Lian et al., Journal of Mol. Biol. 228:1219-1234, 1992) and the crystal structure (see Derrick and Wigley, Journal of Mol. Biol. 243:906-918, 1994) of Protein G have been resolved to 1 Angstrom.

Protein A and Protein G are well-known in the art and commercially available in a variety of conjugated and unconjugated forms.

Also included are functional variants and fragments of full-length or wild-type versions of Protein A and Protein G. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to the wild-type sequence of Protein A and/or Protein G. A functional fragment of can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 450, 500 or more contiguous or non-contiguous residues of wild-type Protein A and/or Protein G. Useful variants and fragments of Protein A and Protein G for purposes of the present invention are those which retain specific binding for the Fc region of one or more immunoglobulin isotypes.

Fusion proteins that comprise Fc-binding polypeptides are also contemplated, including Protein A fusions and Protein G fusions. Fc-binding molecules can be fused to all or a portion of another Fc-binding molecule, or to one or more heterologous polypeptides. A specific example of a Protein A/G fusion protein combines four Fc-binding domains from Protein A with two from Protein G (see, e.g., Sikkema, J. W. D., Amer. Biotech. Lab, 7:42, 1989; and Eliasson et al., J. Biol. Chem. 263, 4323-4327, 1988); however, other combinations can be used. Fusion partners (e.g., a peptide or other moiety) can be used to improve purification, improve solubility, enhance expression of the polypeptide in a host cell, aid in detection, and stabilize the polypeptide, etc. Examples of fusion partners include carrier proteins (e.g., serum albumin such as bovine serum albumin), betagalactosidase, glutathione-S-transferase, histidine tag(s), etc.

In one embodiment, the recombinant spike protein antigen present in the conjugate on the conjugate pad is in a prefusion conformation. SEQ ID NO: 1 represents the amino acid sequence of the wild-type 2019-nCoVS spike structural protein (GenBank No. MN908947). In one particular embodiment, the recombinant spike protein antigen comprises a fragment of the wild-type 2019-nCoVS protein of SEQ ID NO: 1, wherein the fragment comprises the S1 and S2 domains and includes a double proline substitution at positions 986 and 987 of the wild-type protein. In one embodiment, the fragment of the wild-type 2019-nCoVS protein comprising the S1 and S2 domains and including the double proline substitution corresponds to residues 14 to 1208 of the wild-type 2019-nCoVS protein of SEQ ID NO: 1. In another embodiment, the fragment of the wild-type 2019-nCoVS protein comprising the S1 and S2 domains and the double proline substitution further includes a furin cleavage site "GSAS" (SEQ ID NO: 5) at positions 682 to 685 of the wild-type protein. In yet another embodiment, the fragment of the wild-type 2019-nCoVS protein comprising the S1 and S2 domains, the double proline substitution, and the furin cleavage site further comprises a C-terminal T4 fibritin foldon motif "GYIPEAPRGDQAYVRKDGEWVLLSTFL" (SEQ ID NO: 2). In another embodiment, the fragment of the wild-type 2019-nCoVS protein comprising the S1 and S2 domains, the double proline substitution, the furin cleavage site, and the C-terminal T4 fibritin foldon motif further includes a C-terminal polyhistidine tag. In some embodiments, the recombinant SARS-CoV-2 spike protein antigen has the amino acid sequence of SEQ ID NO: 3. As is evident from SEQ ID NO: 3, the N-terminal signal peptide "MFVFLVLLPLVSS" is not present since the gene construct was expressed in mammalian cells.

Also included are functional polypeptide variants or fragments of a recombinant SARS-CoV-2 spike protein antigen of SEQ ID NO: 3. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to SEQ ID NO: 3. A functional fragment of can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 450, 500 or more contiguous or non-contiguous residues of SEQ ID NO: 3. Useful variants and fragments of a recombinant SARS-CoV-2 spike protein antigen of SEQ ID NO: 3 are those which retain specific binding for the SARS-CoV-2 antibodies in the sample.

In one embodiment, the SARS-CoV-2 spike protein antigen employed on the device and in the kit is represented by the amino acid sequence of SEQ ID NO: 3. However, the present invention is not limited as such. For instance, another suitable example of a recombinant spike protein antigen that can be employed in the device and kits of this invention is Spike Ectodomain (ECD) S1/S2 (catalog no. Z03481, GenScript, Piscataway, NJ, USA).

Percent sequence identity has an art recognized meaning and there are a number of methods to measure identity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used, with an affine gap search with a gap open penalty of −12 and a gap extension penalty of −2.

Another aspect of the present invention relates to a diagnostic kit comprising an LF device as described herein. The kit can further include test kit instructions, a non-limiting example of which is shown in FIG. 3.

In some embodiments, the lateral flow device/test can be made to differentiate infected versus vaccinated animals (DIVA) through incorporation of a secondary antigen onto the test. In one embodiment, the secondary antigen is a non-native antigen present in the vaccine (such as recombinant T4 fibritin in FIG. 4). In this example, animals with seroconversion to both the spike protein antigen and the secondary antigen have been vaccinated, whereas seroconversion to only the spike protein antigen indicates infection. Alternatively, the secondary antigen can be a viral protein not incorporated in the vaccine, such as a nucleocapsid or matrix protein of SARS-CoV-2. In this example, animals with seroconversion to both the spike protein antigen and the secondary viral protein have been infected, whereas animals with seroconversion only to the spike protein antigen have been immunized. The secondary antigen may be incorporated onto a second strip housed within the same cassette, containing two sample addition ports and read windows.

In one embodiment of the device, the secondary antigen employed in a DIVA format is deposited on a conjugate pad of the lateral flow device in the form of a conjugate comprising a secondary antigen that has been conjugated to a detection agent, such as, but not limited to, a gold particle. When the device is in operation, the sample flows under capillary action through the strip from the sample pad to the conjugate pad and mobilizes the secondary antigen conjugate contained in the conjugate pad. In another embodiment, the lateral flow device used in a DIVA format includes a detection band comprising an Fc-binding protein immobilized within the test strip, such that in operation when the mobilized secondary antigen conjugate in the sample contacts the Fc-binding protein in the detection band, the presence of antibodies to the secondary antigen in the sample is indicated by a visible color change. However, it is envisioned that a protein other than an Fc-binding protein can be used to capture the formed secondary antigen-antibody complex, as well.

Methods

Also included are methods of detecting antibodies to severe acute respiratory syndrome coronavirus 2 (SARS-CoV-2) in a bodily fluid of an animal or human. This method includes using a lateral flow device according to any of the embodiments described herein.

The present invention also includes a method for the detection of antibodies to SARS-CoV-2 in a sample of bodily fluid of an animal or human, the method including contacting the sample with a conjugate comprising a recombinant SARS-CoV-2 spike protein antigen that has been conjugated to a detection agent, wherein an antigen-antibody complex is formed between the SARS-CoV-2 spike protein antigen conjugate and SARS-CoV-2 antibodies present in the sample; capturing the formed antigen-antibody complex with an Fc-binding molecule; and detecting the captured complex. A non-limiting example of the type of complex that can result from such a method is shown in FIG. 2 where the Fc-binding protein is Protein G and wherein the detection agent is a gold colloid particle.

In one embodiment of the methods, the Fc-binding protein is Protein G, Protein A, or a Protein A/G fusion protein. In another embodiment of the methods, the detection agent conjugated to the SARS-CoV-2 spike protein antigen is selected from metallic nanoparticles or nanoshells, non-metallic nanoparticles or nanoshells, enzymes, or fluorescent molecules. In some preferred embodiments of the methods, the detection agent comprises nanoparticles or nanoshells of metallic gold.

In some embodiments of the methods, the recombinant spike protein antigen is in a prefusion conformation. In one embodiment, the recombinant spike protein antigen employed in the method comprises a fragment of a wild-type 2019-nCoVS protein having the amino acid sequence of SEQ ID NO: 1, wherein the fragment comprises the S1 and S2 domains and includes a double proline substitution at positions 986 and 987 of the wild-type protein. In another embodiment of the methods, the fragment comprising the S1 and S2 domains and the double proline substitution corresponds to residues 14 to 1208 of the wild-type 2019-nCoVS protein. In yet another embodiment of the methods, the fragment of the wild-type 2019-nCoVS protein comprising the S1 and S2 domains and the double proline substitution further includes a furin cleavage site "GSAS" (SEQ ID NO: 5) at positions 682 to 685 of the wild-type protein. In still further embodiments of the methods, the fragment of the wild-type 2019-nCoVS protein comprising the S1 and S2 domains, the double proline substitution, and the furin cleavage site further comprises a C-terminal T4 fibritin foldon motif "GYIPEAPRGDQAYVRKDGEWVLLSTFL" (SEQ ID NO: 2). In another embodiment, the fragment of the wild-type 2019-nCoVS protein comprising the S1 and S2 domains, the double proline substitution, the furin cleavage site, and the C-terminal T4 fibritin foldon motif further includes a C-terminal polyhistidine tag.

In some embodiments, the recombinant SARS-CoV-2 spike protein antigen employed in the methods of this invention has the amino acid sequence of SEQ ID NO: 3. As is evident from SEQ ID NO: 3, the N-terminal signal peptide "MFVFLVLLPLVSS" is not present since the gene construct was expressed in mammalian cells.

The methods of the present invention are not limited to the use of a spike protein antigen represented by SEQ ID NO: 3. For instance, another suitable example of a recombinant spike protein antigen that can be employed in the methods of this invention is Spike Ectodomain (ECD) S1/S2 (catalog no. Z03481, GenScript, Piscataway, NJ, USA).

The methods described herein can be made to differentiate infected vs vaccinated animals (DIVA), if desired. For example, the methods can be made to further include contacting the sample with a conjugate comprising a secondary antigen, such as a non-native antigen incorporated in the SARS-CoV-2 vaccine. The non-native antigen is conjugated to a detection agent. In this embodiment, an antigen-antibody complex is formed between the non-native antigen and any antibodies present in the sample that may have developed in the animal or human against the non-native antigen following vaccination. In one embodiment, the formed secondary antigen-antibody complex is captured with an Fc-binding molecule, for example; and the captured complex is detected. In this example, animals with seroconversion to both the spike protein antigen and the non-native antigen have been vaccinated, whereas seroconversion to only the spike protein indicates infection. It is envisioned that a protein other than an Fc-binding protein can be used to capture the formed secondary antigen-antibody complex, as well.

Alternatively, the secondary antigen included as part of a DIVA method can be a viral protein not incorporated in the vaccine. For example, the methods described herein can include contacting the sample with a conjugate comprising a secondary viral protein such as a nucleocapsid or matrix protein of SARS-CoV-2. The secondary viral protein is conjugated to a detection agent. In this embodiment, an antigen-antibody complex is formed between the secondary viral protein and any antibodies present in the sample that may have developed in the human or animal against the secondary viral protein as a result of infection with SARS-CoV-2. In one embodiment, the formed antigen-antibody complex is captured with an Fc-binding molecule, for example; and the captured complex is detected. In this example, animals with seroconversion to both the spike protein and the viral protein not incorporated in the vaccine have been infected, whereas animals with seroconversion only to spike protein have been immunized. It is envisioned that a protein other than an Fc-binding protein can be used to capture the formed secondary antigen-antibody complex, as well.

The invention is further described with reference to the following examples. It will be appreciated that the invention as claimed is not intended to be limited in any way by these examples.

EXAMPLES

Example 1

The present example describes the process for engineering, transformation and purification of the recombinant SARS-CoV-2 spike protein antigen which is conjugated to a detection agent and used in the diagnostic device and method of the present invention. To express the SARS-CoV-2 spike ectodomain, a gene construct was designed using GenBank MN908947.3 as a template. The construct contains sequence corresponding to amino acid residues 1-1208 of 2019-n-COV S protein containing a furin cleavage site knockout (residues 682-685), proline mutations at residues 986-987, a C-terminal T4 Fibritin trimerization motif and a 6× polyhistidine tag. The construct was codon optimized for CHO expression and synthesized by GeneArt. The resulting construct was cloned into pcDNA3.1 (+) for mammalian expression. Suitable cloning methods are described in D. Wrapp et al., Science 10.1126/Science.abb2507 (2020) and/or in WO2018/081318 A1, the entire contents each of which are incorporated herein by reference in their entirety.

The expression vector was transiently transfected into HEK293F cells (Thermo Fisher Scientific™) using Fecto-Pro transfection reagent (Polyplus). After 7 days of expression, the cells were removed by centrifugation and the supernatants filtered. The protein was purified using Ni sepharose Excel resin (GE Life Sciences). Briefly, 5 mM imidazole was added to the supernatants, and 1 ml of 50% resin pre-washed and resuspended in 50 mM Tris-HCl (pH 7.5)+300 mM NaCl buffer was added to the supernatant for overnight batch binding at 4 C. The next morning, the supernatants were transferred to Biorad disposable columns and washed 2×5 mls of wash buffer (50 mM Tris-HCl (pH 7.5); 300 mM NaCl; 20 mM imidazole. The protein was then eluted in 2 ml of elution buffer (50 mM Tris-HCl (pH 7.5); 300 mM NaCl; 250 mM imidazole. The eluate was dialyzed against 3×1000 ml of dialysis buffer (50 mM Tris-HCl (pH 7.5); 300 mM NaCl) and stored at 4 C.

The sequence of the recombinantly expressed mature SARS-CoV-2 spike protein antigen is shown in FIG. 4 and corresponds to SEQ ID NO: 3. In FIG. 4, the furin cleavage site knockout "GSAS" (SEQ ID NO: 5) and the double proline substitution "PP" are each underlined and in bold print. Also, in FIG. 4, the C-terminal T4 Fibritin trimerization motif is shown with dashed underlining and the 6× polyhistidine tag is double-underlined.

Example 2

The present example describes one embodiment of the device and method of the present invention. The tests consists of a nitrocellulose membrane laminated to an adhesive backing card. Both ends of the nitrocellulose membrane are overlapped by an adjacent conjugate pad and an adjacent absorption pad. A blood separation sample pad overlaps the conjugate pad. After deposition of all reagents to the respective membranes, the card is cut into strips approximately 6 mm-wide, and assembled into a plastic housing with a sample addition port over the sample pad, and a reading window over the nitrocellulose membrane.

To perform the test, a drop (~25 μL) of whole blood, serum, or plasma is added to the sample port. Two drops of a chase buffer are then added to the sample port. Specific antibodies in the sample will migrate to the conjugate pad and react with recombinant SARS-CoV-2 Spike protein conjugated to colloidal gold. The antibody-Spike protein-gold complex migrates across the nitrocellulose where the complexed antibody is immobilized by Protein A or G deposited on the test line. The accumulation of colloidal gold particles on the test line form a visible red line if antibodies are present, indicating a positive result. If anti-SARS-CoV-2 spike antibodies are not present in the sample, the gold conjugate is not immobilized on the test line and continues to migrate to the absorbent pad. The lack of formation of a red line on the test line indicates the sample is negative for antibodies to SARS-CoV-2. A second conjugate deposited onto the conjugate pad—a control conjugate—consists of chicken IgY conjugated to colloidal gold. The control conjugate migrates across the nitrocellulose upon addition of sample and chase buffer and is immobilized on a second reaction line—the control line—by an anti-chicken IgY antibody. The accumulation of colloidal gold control conjugate particles forms a red control line. The control line is a procedural control and indicates the test was performed correctly and flowed correctly. Test results are interpreted after 10 minutes.

The conjugation can be prepared using standard protein conjugation methods to colloidal gold. The protein is mixed with a buffer at a desired pH. The colloidal gold (sourced commercially) is added to the protein and mixed for 5-10 minutes. A second basic buffer is added to the conjugate to raise the pH, and the conjugate is blocked by the addition of BSA.

To prepare the control conjugate, colloidal gold is adjusted to a desired pH. A saturating quantity of protein between 20 and 100 μg/ml gold is added to the gold and incubated for 10 minutes. A BSA blocker is then added to the gold and incubated for an additional 10 minutes. A stabilizer buffer including BSA and sucrose is added to the conjugate.

The conjugates are mixed together at a critical, optimized OD with a conjugate diluent consisting of detergents, buffer, sucrose, and BSA. The conjugates are sprayed onto the conjugate pad with an airjet sprayer.

The test and control line reagents, Protein A or G, and Donkey anti-chicken IgY, respectively, are diluted to an optimized, critical concentration in a deposition buffer with stabilizing sugars. The reagents are deposited onto the nitrocellulose with a high precision fluidic handler, capable of spraying micro quantities of volume. The cards are cured for 4 days at 37° C. and then stored at <30% relative humidity.

The chase buffer is formulated with a blocker protein such as BSA, a buffer to maintain pH, Tween 20, sodium azide, and polyethylene glycol (PEG) 8000.

Example 3

Data and Validation Studies

Canine, feline, mink, and human specimens were tested on the LFA to determine diagnostic performance. All samples were read visually and on a lateral flow strip reader (Detekt RDS 2500). The reader generates a quantitative densitometric value for the intensity of the test line based on image analysis. The final result for canine, feline, and mink tests is determined by visual observation whereas the human test result is determined by the reader, using a positive cut-off value of 33,769. Visual results were recorded as:

(−): negative; no test line visible (+/−): very faint positive; test line visible as a shadow or ghost line (+): weak positive but test line is clearly visible (++): moderately strong positive (+++): strong positive; test line intensity as strong as the control line (++++): very strong positive; test line intensity stronger than control line

Canine

A total of 635 canine serum samples were tested to determine diagnostic performance in dogs.

To assess specificity, 615 seronegative canine serum samples were tested from healthy dogs or dogs infected with common canine respiratory diseases, including canine influenza, *Bordetella bronchiseptica*, or canine parainfluenza. The specificity also includes the saline controls from Vaccine Study 2, and the pre-vaccination samples from Vaccine Studies 1 and 2. Specificity was 95.4% (587/615). Data are summarized in Table 1 below.

TABLE 1

| Specificity | Test Neg/True Neg | % Specificity |
|---|---|---|
| SPF/Vaccine Study pre-bleeds and controls | 137/146 | 93.8% |
| Canine Influenza | 57/59 | 96.6% |
| Bordetella | 55/60 | 91.7% |
| Canine Parainfluenza | 48/49 | 98.0% |
| Pre-Covid/Client Owned Field | 290/301 | 96.3% |
| Total | 587/615 | 95.4% |

To determine sensitivity, sera were collected from dogs in two different SARS-CoV-2 vaccination studies (n=16) or reference lab submissions with suspected infection or exposure to SARS-CoV-2 (n=4). All 20 samples were positive on LFA. Study design and results of the individual studies are described below.

Example 4

Canine Vaccine Study #1

Six dogs randomized into 3 treatment groups were vaccinated with different formulations of a recombinant SARS-CoV-2 spike protein antigen (CRM197:Receptor binding domain (RBD) Conjugate (T01; RBD portion is catalog no. Z04383, GenScript, Piscataway, NJ, USA); Spike Ectodomain (ECD) S1/S2 (T02; catalog no. Z03481, GenScript, Piscataway, NJ, USA); RBD:IgG FC Fusion (T03; catalog no. Z03491, GenScript, Piscataway, NJ, USA)).

Dogs were vaccinated on days 0, 21, and 42. Sera were collected on Days 0, 15, 21, and 28. Four of 6 dogs were negative on the LFA on day 0 with two dogs testing false positive from cross-reactivity, and all dogs were positive on the LFA by day 28. The two dogs that tested false positive on day 0 showed a substantial increase in test signal by day 28 after receiving immunizations. The results of vaccine study 1 are presented below in Table 2.

TABLE 2

| Treatment Group | Sample | Day 0 | | Day 15 | | Day 21 | | Day 28 | |
|---|---|---|---|---|---|---|---|---|---|
| (C6344) | ID | Visual | Reader | Visual | Reader | Visual | Reader | Visual | Reader |
| T01 | 3886914 | − | 6,240 | − | 5,318 | − | 14,028 | ++++ | 594,604 |
| T01 | 3888178 | + | 108,895 | +/− | 73,891 | +/− | 18,218 | ++++ | 376,164 |
| T02 | 3888828 | − | 7,372 | +++ | 687,740 | +++ | 659,764 | ++ | 645,921 |
| T02 | 3888232 | +/− | 18,340 | +++ | 872,770 | +++ | 757,040 | ++++ | 417,912 |
| T03 | 3889612 | − | 8,943 | +++ | 739,584 | +++ | 805,613 | ++++ | 781,166 |
| T03 | 3889140 | − | 7,465 | +++ | 875,217 | +++ | 540,103 | +++ | 895,984 |

Example 5

Canine Vaccine Study #2

Fifteen dogs were randomized into three treatment groups (n=5 per treatment group). Treatment group T01 (Saline) dogs were placebo controls whereas groups T02 (recombinant Spike protein; Rehydragel adjuvant) and T03 (recombinant Spike protein, QCT adjuvant) received a recombinant SARS-CoV-2 spike protein vaccine with different adjuvant formulations. Dogs were vaccinated on study days 0 and 21 and sera were collected on study days 0, 21, and 42. Sera from each study day were tested on LFA. All dogs were negative on day 0. LFA results were positive for all dogs in T02 and T03 on study days 21 and 42, while sera from control dogs in T01 produced negative results at all timepoints. Data are listed in Table 3 below.

TABLE 3

| Sensitivity | | Day 0 | | Day 21 | | Day 42 | |
|---|---|---|---|---|---|---|---|
| (B6478) | Sample | Visual | Reader | Visual | Reader | Visual | Reader |
| T01 | 6586279 | − | 5,965 | − | 3,411 | − | 5,571 |
| T01 | 6586384 | − | 9,728 | − | 11,932 | − | 4,243 |
| T01 | 6586457 | − | 6,676 | − | 6,952 | − | 5,706 |
| T01 | 6591183 | − | 4,249 | − | 10,458 | − | 6,727 |
| T01 | 6591558 | − | 4,955 | − | 4,010 | − | 7,843 |
| T02 | 6586287 | − | 5,497 | +/− | 20,082 | ++++ | 850,922 |

TABLE 3-continued

| Sensitivity (B6478) | Sample | Day 0 Visual | Day 0 Reader | Day 21 Visual | Day 21 Reader | Day 42 Visual | Day 42 Reader |
|---|---|---|---|---|---|---|---|
| T02 | 6586341 | – | 1,903 | +++ | 365,099 | ++++ | 908,487 |
| T02 | 6586490 | – | 5,431 | +++ | 295,387 | ++++ | 749,547 |
| T02 | 6590969 | – | 10,843 | ++++ | 650,084 | ++++ | 964,848 |
| T02 | 6591094 | – | 10,884 | + | 132,687 | ++++ | 775,755 |
| T03 | 6586295 | – | 1,567 | +++ | 558,603 | ++++ | 757,122 |
| T03 | 6586350 | – | 3,582 | +++ | 695,001 | ++++ | 935,679 |
| T03 | 6586422 | – | 3,675 | +++ | 556,414 | ++++ | 985,040 |
| T03 | 6591442 | – | 10,982 | +++ | 541,499 | ++++ | 727,335 |
| T03 | 6591540 | – | 6,998 | ++++ | 755,504 | ++++ | 793,830 |

Example 6

Reference Lab Samples

Five canine field samples submitted to Zoetis reference labs with suspicion of SARS-CoV-2 infection were tested on the LFA and a virus neutralization (VN) assay. All five dogs were positive on LFA, whereas only four were positive on VN. The results are summarized below.

TABLE 4

| Name | Breed | PCR | Serology | Confirmation |
|---|---|---|---|---|
| Buddy | German shepherd | Pos | Pos | PCR Pos<br>VN Pos 512 |
| Duke | German shepherd | Neg | Pos | PCR Neg<br>VN Pos 32 |
| Bao | Maltese | Neg | Pos | PCR Neg<br>VN Neg |
| Bene | Pitbull | Neg | Pos | PCR Neg<br>VN Pos 32 |
| Nene | Maltese | Neg | Pos | PCR Neg<br>VN Pos 64 |

Conclusions:

As a test for detection of antibodies to SARS-CoV-2 in dogs, the LFA was highly specific (95.4%, n=615) and sensitive (100%, n=20). The test delivered correct results for 607 of 635 canine samples, for an accuracy of 95.6%.

Example 7

Feline Test Results

A total of 744 feline serum samples were tested to determine diagnostic performance in cats.

To assess specificity, 716 presumed seronegative feline serum samples were tested from healthy cats or cats infected or vaccinated with feline leukemia virus (FeLV), feline immunodeficiency virus (FIV), *Toxoplasma gondii*, feline coronavirus (feline infectious peritonitis; FIP), or feline herpesvirus-panleukopenia-calicivirus-FeLV combination vaccine. The specificity also includes the saline controls and the pre-vaccination samples from Vaccine Studies 1 and 2. Specificity was 93.7% (671/716). Data are summarized in Table 5 below.

TABLE 5

| Sample | Test Neg/True Neg | Specificity |
|---|---|---|
| SPF, vaccine study pre-bleeds and controls | 116/117 | 99.2% |
| FeLV/FIV Positive (field and challenge) | 165/173 | 95.4% |
| FVRCP Vaccinated Animals (Rhino, Calici, PanLeuk, FeLV) | 80/80 | 100% |
| Toxoplasmosis | 2/2 | 100% |
| Feline Coronavirus (FIP) | 36/45 | 80.0% |
| Pre-Covid Client Owned Samples | 272/299 | 91.0% |
| Total | 671/716 | 93.8% |

To assess assay sensitivity, sera were collected from cats in two different SARS-CoV-2 vaccination studies (n=28). All samples were positive on LFA (100% sensitivity). Study design and results of the individual studies are described below.

Example 8

Feline Vaccine Study #1

Fifteen cats were randomized into three treatment groups (n=5 per treatment group). Treatment group T01 (saline) cats were placebo controls whereas groups T02 (recombinant Spike protein; QCDC adjuvant) and T03 (recombinant Spike protein; RT adjuvant) received a recombinant SARS-CoV-2 spike protein vaccine with different adjuvant formulations. Cats were vaccinated on study days 0 and 21, and sera were collected on study days 0, 21, and 42. Sera from each study day were tested on LFA. All cats were negative on day 0. LFA results were positive for all cats in T02 and T03 on study days 21 and 42, while sera from control cats in T01 produced negative results at all timepoints. Data are listed in Table 6 below.

TABLE 6

| Sensitivity (B8115) | Sample ID | Day 0 Visual | Day 0 Reader | Day 21 Visual | Day 21 Reader | Day 42 Visual | Day 42 Reader |
|---|---|---|---|---|---|---|---|
| T01 | M191962 | – | 8,973 | – | 9,288 | – | 10,309 |
| T01 | M191610 | – | 9,545 | – | 10,443 | – | 11,800 |
| T01 | M192021 | – | 9,169 | – | 5,292 | – | 7,804 |
| T01 | M191687 | – | 11,614 | – | 7,924 | – | 17,164 |
| T01 | M191814 | – | 5,862 | – | 14,558 | – | 12,855 |
| T02 | M191628 | – | 7,526 | +++ | 188,166 | +++ | 521,160 |
| T02 | M191644 | – | 10,431 | +++ | 293,915 | +++ | 342,056 |
| T02 | M191733 | – | 10,775 | +++ | 221,439 | +++ | 401,849 |
| T02 | M191776 | – | 14,205 | ++ | 247,635 | +++ | 462,343 |
| T02 | M191989 | – | 5,853 | ++ | 226,459 | +++ | 411,664 |
| T03 | M191602 | – | 7,066 | +/– | 20,709 | +++ | 363,478 |
| T03 | M191725 | – | 9,878 | + | 142,507 | +++ | 375,131 |
| T03 | M191857 | – | 14,056 | ++ | 243,948 | +++ | 252,345 |

TABLE 6-continued

| | | Day 0 | | Day 21 | | Day 42 | |
|---|---|---|---|---|---|---|---|
| Sensitivity (B8115) | Sample ID | Visual | Reader | Visual | Reader | Visual | Reader |
| T03 | M191920 | – | 6,730 | + | 164,120 | +++ | 438,883 |
| T03 | M192004 | – | 11,400 | ++ | 157,025 | +++ | 540,735 |

Example 9

Feline Vaccine Study #2

Twenty-four cats were randomized into four treatment groups (n=6 per treatment group). Treatment group T01 (saline) cats were placebo controls, groups T02 (recombinant Spike protein; QCDC adjuvant), and T03 (a chimpanzee adenovirus vaccine (ChAdOx1 nCoV-19) expressing the SARS-CoV-2 spike protein) received the respective formulations of the SARS-CoV-2 vaccine on study days 0 and 21, and treatment group T04 received the same vaccine as treatment group T03 but were vaccinated only on study day 0, without a booster on day 21. Sera were collected on study days-1, 21, and 42. Sera from each study day were tested on LFA. All cats were negative on day-1. LFA results were positive for all cats in T02-T04 on study days 21 and 42, while sera from control cats in T01 produced negative results at all timepoints. Data are listed in Table 7 below.

TABLE 7

| | | Day −1 | | Day 21 | | Day 42 | |
|---|---|---|---|---|---|---|---|
| Sensitivity (B8119) | Sample | Visual | Reader | Visual | Reader | Visual | Reader |
| T01 | M191474 | – | 8,733 | – | 12,910 | – | 12,692 |
| T01 | M191539 | – | 11,032 | – | 7,191 | – | 16,513 |
| T01 | M192110 | – | 13,175 | – | 7,158 | – | 12,064 |
| T01 | M192144 | – | 7,017 | – | 10,637 | – | 11,576 |
| T01 | M192790 | – | 10,247 | – | 7,186 | – | 10,487 |
| T01 | M194474 | – | 9,699 | – | 6,898 | – | 11,731 |
| T02 | M191679 | – | 10,811 | +++ | 410,522 | +++ | 269,047 |
| T02 | M191806 | – | 13,506 | +++ | 210,551 | +++ | 641,472 |
| T02 | M191849 | – | 12,520 | +++ | 353,683 | +++ | 375,325 |
| T02 | M192128 | – | 6,648 | ++ | 138,759 | +++ | 491,938 |
| T02 | M192812 | – | 8,047 | ++ | 181,299 | +++ | 345,383 |
| T02 | M194229 | – | 11,536 | +++ | 273,609 | +++ | 384,670 |
| T03 | M191423 | – | 13,274 | +++ | 259,927 | +++ | 407,319 |
| T03 | M191512 | – | 8,654 | +++ | 353,786 | +++ | 498,557 |
| T03 | M191661 | – | 11,233 | +++ | 246,680 | +++ | 352,282 |
| T03 | M192102 | – | 11,589 | +++ | 326,300 | +++ | 464,607 |
| T03 | M193079 | – | 11,680 | +++ | 404,100 | +++ | 516,580 |
| T03 | M193184 | – | 7,417 | +++ | 311,781 | +++ | 550,332 |
| T04 | M191547 | – | 9,694 | +++ | 337,483 | ++ | 257,015 |
| T04 | M191555 | – | 9,422 | +++ | 359,769 | ++ | 367,796 |
| T04 | M191792 | – | 1,347 | +++ | 235,350 | ++ | 250,686 |
| T04 | M192136 | – | 13,368 | +++ | 486,705 | +++ | 497,748 |
| T04 | M192871 | – | 10,007 | +++ | 335,750 | +++ | 493,778 |
| T04 | M194483 | – | 15,597 | ++ | 157,694 | ++ | 185,494 |

Conclusions:

As a test for detection of antibodies to SARS-CoV-2 in cats, the LFA was highly specific (93.8%, n=716) and sensitive (100%, n=28). The test delivered correct results for 699 of 744 samples, for an accuracy of 94.0%.

Example 10

Human Serology Study #1

Human plasma samples (n=47) collected from humans with positive confirmation of COVID-19 by PCR (CDC method) and ELISA (Promega) and 78 pre-pandemic (collected November 2020 or earlier) human plasma samples (n=78) with negative confirmation by the same methods were tested on the LFA. Data are listed in Table 8 below.

TABLE 8

| | Correct Results | Total No. Samples | Estimated Performance | 95% Confidence Interval |
|---|---|---|---|---|
| Sensitivity | 44 | 47 | 93.6% | 82.5-98.7% |
| Specificity | 76 | 77 | 98.7% | 92.9-100% |

Example 11

Human Serology Study #2

To demonstrate compatibility with whole blood sample matrix, blood samples from 30 healthy seronegative donors were collected in EDTA (n=10), sodium heparin (n=8-10), or citrate (n=10) anticoagulant blood tubes were spiked with 30 unique COVID-19-positive plasma samples from Example 10 (one plasma sample per blood sample). To spike the blood, a volume of blood was centrifuged, and a volume of plasma was removed and replaced with an equal volume of positive plasma. The blood was carefully resuspended. Each blood sample, except for two samples from the sodium heparin anticoagulant condition, was also tested without addition of a spike.

All tests yielded the expected result, summarized in Table 9 below.

TABLE 9

| | Correct Results | Total No. Samples | Estimated Performance |
|---|---|---|---|
| Sensitivity (spiked) | 30 | 30 | 100% |
| Specificity (un-spiked) | 28 | 28 | 100% |

Conclusions:

As a test for detection of antibodies to SARS-CoV-2 in humans, the LFA was highly specific (99.1%, total n=106) and sensitive (93.6%, n=47). The test was compatible with plasma and whole blood matrices in three different anticoagulants. The test delivered correct results for 149 of 153 unique samples, for an accuracy of 97.4%.

Example 12

Human Serology Study #3

To verify that the test does not cross-react with other common infectious agents of humans, 118 plasma sample specimens were tested from humans antibody positive for Influenza A, Influenza B, Hepatitis B and C virus, *Haemophilus influenzae*, Alpha coronavirus 229E, Alpha coronavirus NL63, Beta coronavirus OC43, Beta coronavirus HKU1, Respiratory Syncytial Virus, and Human Immunodeficiency Virus (HIV). An additional 41 samples from healthy humans collected November 2019 or earlier (pre-pandemic) were tested to further build out the specificity data. A final 23 samples were tested from patients with a positive confirmation of COVID-19 and a collection date 0-7 days (n=7) and 8-13 days (n=10), and ≥30 days post-onset of symptoms; the latter samples were tested as 'positive controls' as they were very likely to be positive on the LFA.

Exclusive specificity data are summarized in the table below. All samples tested negative.

TABLE 10

| | Correct result | Total No. Samples | Estimated Performance | 95% CI |
|---|---|---|---|---|
| Pre-COVID samples | 40 | 40 | 100% | 91.2-100 |
| Exclusive samples | 54 | 54 | 100% | 93.4-100 |
| Total | 94 | 94 | 100% | 96.2-100 |

Example 13

Human Serology Study #4

To determine diagnostic performance of blood collected via fingerstick and verify its equivalency to blood collected by venous puncture, venous blood and finger stick blood were collected from 37 volunteers with previous history of PCR-confirmed COVID and 38 volunteers with no known previous COVID. A plasma sample from the venous whole blood fraction from each donor was tested on an FDA Emergency Use Authorization (EUA)-approved serological method (ELISA) to serve as the reference method.

Of the 37 volunteers with previous PCR-confirmed diagnosis of COVID, 30 were positive on the reference ELISA. Two readings were not captured by the machine reader for venous blood, resulting in only 28 results. The seven seronegative results were included in the specificity calculation. Three specificity readings were not captured by the machine reader for venous blood, resulting in 42 results to report. Diagnostic performance was similar for fingerstick and venous blood. Results are summarized in Tables 11, 12, and 13 below.

TABLE 11

| Sensitivity (ELISA as reference) | | | | |
|---|---|---|---|---|
| | Number of | Candidate Device Results | | |
| Blood Source | Samples Tested | Total Antibody Positive Results | Sensitivity | 95% CI |
| Fingerstick | 30 | 29 | 29/30 (96.7%) | 82.8-99.9 |
| Venous | 28 | 28 | 28/28 (100%) | 87.7-100 |

TABLE 12

| Specificity (ELISA as reference) | | | | |
|---|---|---|---|---|
| | Number of | Candidate Device Results | | |
| Blood Source | Samples Tested | Total Antibody Negative Results | Specificity | 95% CI |
| Fingerstick | 45 | 44 | 44/45 (97.8%) | 88.2-99.9 |
| Venous | 42 | 42 | 42/42 (100%) | 91.6-100 |

TABLE 13

| Acreemen between blood source. | | | | |
|---|---|---|---|---|
| | Number of | Candidate Device Results | | |
| | Samples Tested | Number of Results in Agreement | Agreement (%) | 95% CI |
| Positive Percent Agreement | 28 | 27 | 27/28 (96.4%) | 81.7-99.9 |
| Negative Percent Agreement | 42 | 41 | 41/42 (97.6%) | 87.4-99.9 |

Example 14

Mink Serology Study

Twenty (20) seronegative mink of approximately 6 months of age were randomly allocated into three vaccine treatment groups: T01-true placebo with 4 animals, T02-double dose of an adjuvanted recombinant trimeric spike protein with 8 animals and T03 single dose of the same vaccine with 8 animals. The study design was in accordance with the dosing regimen for the SARS COV-2 recombinant vaccine which is 2 doses given 3 weeks apart. Sera from all mink were tested on the LFA in a double cassette featuring Protein A and Protein G versions of the test, on study day 0, 21, and 42.

All animals had negative LFA on Day 0 for both strips. On Days 21 and 42, the control group remained negative, but all the animals in the two vaccinated groups, T02 (double dose) and T03 (single dose), were positive on both LFA strips.

TABLE 14

| Protein A-based LFA results with mink sera. | | | | | | | |
|---|---|---|---|---|---|---|---|
| | | Day of Study | | | | | |
| | | 0 | | 21 | | 42 | |
| Treat-ment | Animal | Result (visual) | Reader | Result (visual) | Reader | Result (visual) | Reader |
| T01 | 11 | negative | 23751 | negative | 15451 | negative | 18100 |
| | 14 | negative | 15647 | negative | 19636 | negative | 17668 |
| | 6 | negative | 8564 | negative | 10913 | negative | 15581 |
| | 7 | negative | 20075 | negative | 9517 | negative | 15231 |
| T02 | 1 | negative | 4411 | positive | 303367 | positive | 614020 |
| | 10 | negative | 17050 | positive | 190156 | positive | 442534 |
| | 16 | negative | 17256 | positive | 289406 | positive | 671792 |
| | 17 | negative | 9432 | positive | 183245 | positive | 446019 |
| | 19 | negative | 20802 | positive | 171364 | positive | 421605 |
| | 20 | negative | 17647 | positive | 128134 | positive | 545932 |
| | 3 | negative | 6996 | positive | 374755 | positive | 646927 |
| | 5 | negative | 19546 | positive | 166698 | positive | 693718 |
| T03 | 12 | negative | 5967 | positive | 141034 | positive | 746350 |
| | 13 | negative | 22217 | positive | 40923 | positive | 458865 |
| | 15 | negative | 17365 | positive | 163492 | positive | 618032 |
| | 18 | negative | 6805 | positive | 176648 | positive | 703228 |
| | 2 | negative | 13555 | positive | 373969 | positive | 728756 |
| | 4 | negative | 11729 | positive | 259594 | positive | 645922 |
| | 8 | negative | 8803 | positive | 209504 | positive | 747389 |
| | 9 | negative | 22487 | positive | 54642 | positive | 340063 |

TABLE 15

| Protein G-based LFA results with mink sera | | | | | | | |
|---|---|---|---|---|---|---|---|
| | | Day of the study | | | | | |
| | | Day 0 | | Day 21 | | Day 42 | |
| Treatment | Animal | Result (visual) | Value | Reader | Value | Result (visual) | Reader |
| T01 | 11 | negative | 5666 | negative | 3025 | negative | 4114 |
| | 14 | negative | 3708 | negative | 5101 | negative | 4453 |
| | 6 | negative | 3070 | negative | 2161 | negative | 2750 |
| | 7 | negative | 3598 | negative | 7335 | negative | 4761 |
| T02 | 1 | negative | 23386 | positive | 290922 | positive | 403041 |
| | 10 | negative | 3382 | positive | 203596 | positive | 301984 |
| | 16 | negative | 4392 | positive | 251196 | positive | 186182 |
| | 17 | negative | 3348 | positive | 180897 | positive | 267824 |
| | 19 | negative | 2641 | positive | 298999 | positive | 346405 |
| | 20 | negative | 4034 | positive | 178410 | positive | 190087 |
| | 3 | negative | 7449 | positive | 328611 | positive | 228808 |
| | 5 | negative | 2359 | positive | 345101 | positive | 215705 |
| T03 | 12 | negative | 1437 | positive | 249759 | positive | 385584 |
| | 13 | negative | 7527 | positive | 170543 | positive | 371627 |
| | 15 | negative | 2562 | positive | 151188 | positive | 260239 |
| | 18 | negative | 3001 | positive | 185040 | positive | 102056 |
| | 2 | negative | 2840 | positive | 241471 | positive | 332223 |
| | 4 | negative | 3602 | positive | 193490 | positive | 305538 |
| | 8 | negative | 2125 | positive | 227510 | positive | 160379 |
| | 9 | negative | 6906 | positive | 191254 | positive | 287303 |

What is claimed is:

1. A lateral flow device for the detection of antibodies to severe acute respiratory syndrome coronavirus 2 (SARS-CoV-2) in a sample of bodily fluid of an animal or human, the device comprising: a) a strip formed of a material enabling capillary flow of fluid along a portion of the strip; b) a sample pad located proximal to one end of the strip for receiving the sample of the bodily fluid, c) a conjugate pad located in the strip so that in operation the sample flows under capillary action through the strip from the sample pad to the conjugate pad and mobilizes a conjugate contained in the conjugate pad, the conjugate comprising a recombinant SARS-CoV-2 spike (S) protein antigen that has been conjugated to a detection agent, and d) a detection band comprising an Fc-binding protein immobilized within the strip along a band located perpendicular to the direction of flow of the sample along the strip so that when the mobilized spike protein conjugate in the sample contacts the Fc-binding protein in the detection band the presence of the antibodies to the SARS-CoV-2 virus in the sample is indicated by a visible color change, wherein the recombinant SARS-CoV-2 spike (S) protein antigen in c) is in a prefusion conformation and comprises a fragment of a wild-type SARS-CoV-2 protein having the amino acid sequence of SEQ ID NO: 1, wherein the fragment comprises the S1 and S2 domains and includes a double proline substitution at positions 986 and 987 of the wild-type protein and wherein the fragment further comprises a furin cleavage site "GSAS (SEQ ID NO: 5)" at positions 682 to 685 of the wild-type protein and a C-terminal T4 fibritin foldon motif "GYIPEAPRGDQAYVRKDGEWVLLSTFL" (SEQ ID NO: 2).

2. The device of claim 1, further comprising a wicking pad for receiving and retaining sample after passing through the detection band.

3. The device of claim 1, wherein the Fc-binding protein is Protein G, Protein A, or a Protein A/G fusion protein.

4. The device of claim 1, wherein the detection agent conjugated to the SARS-CoV-2 spike (S) protein antigen is selected from the group comprising metallic nanoparticles or nanoshells, non-metallic nanoparticles or nanoshells, enzymes, and fluorescent molecules.

5. The device of claim 1, wherein the detection agent comprises nanoparticles or nanoshells of metallic gold.

6. The device of claim 1, wherein the fragment corresponds to residues 14 to 1208 of the wild-type SARS-CoV-2 protein.

7. The device of claim 1, wherein the sample pad comprises a filter membrane for removing one or more components from the sample.

8. The device of claim 7, wherein the one or more components removed from the sample by the filter membrane of the sample pad are cells, cellular material, fats, or particulate matter.

9. The device of claim 1, further comprising a control line located perpendicular to the direction of flow of the sample along the strip.

10. The device of claim 9, wherein deposited on the control line is an antibody capable of capturing any excess mobilized spike (S) protein conjugate as it crosses the control line, said binding at the control line being indicated by a visible color change.

11. The device of claim 10, wherein the antibody capable of capturing any excess spike protein conjugate is a monoclonal antibody which specifically binds the spike protein antigen in the spike (S) protein conjugate.

12. The device of claim 9, wherein the conjugate pad further comprises an immunoglobulin conjugated to a detection agent so that in operation the sample flows from the sample pad to the conjugate pad and mobilizes the immunoglobulin conjugate which passes over the detection band without reactivity and crosses the control line.

13. The device of claim 12, wherein deposited at the control line is an antibody capable of binding to the mobilized immunoglobulin conjugate as it crosses the control line, said binding at the control line being indicated by a visible color change.

14. The device of claim 12, wherein the immunoglobulin in the conjugate is from animal species other than the species from which the sample of bodily fluid is derived.

15. The device of claim 12, wherein the detection agent conjugated to the immunoglobulin is selected from the group comprising metallic nanoparticles or nanoshells, non-metallic nanoparticles or nanoshells, enzymes, and fluorescent molecules.

16. The device of claim 15, wherein the detection agent conjugated to the immunoglobulin comprises nanoparticles or nanoshells of metallic gold.

17. The device of claim 1, wherein the strip is formed of nitrocellulose.

18. The device of claim 1, wherein the sample of bodily fluid is from an animal selected from the group consisting of a canine, a feline, equine, caprine, murine, avian, ovine, bovine, or a mustelid animal.

19. The device of claim 1, wherein the sample of bodily fluid is from a human.

20. The device of claim 1, wherein the bodily fluid is selected from the group comprising whole blood, blood serum, blood plasma, mucous, saliva, and urine.

21. A method for the detection of antibodies to severe acute respiratory syndrome coronavirus 2 (SARS-CoV-2) in a bodily fluid of an animal or human comprising using a device of claim 1.

22. A method for the for the detection of antibodies to severe acute respiratory syndrome coronavirus 2 (SARS-CoV-2) in a sample of bodily fluid of an animal or human, the method comprising contacting the sample with a conjugate comprising a recombinant SARS-CoV-2 spike (S) protein antigen that has been conjugated to a detection agent, wherein an antigen-antibody complex is formed between the SARS-CoV-2 spike (S) protein antigen conjugate and SARS-CoV-2 antibodies present in the sample; capturing the formed antigen-antibody complex with an Fc-binding molecule; and detecting the captured complex, wherein the recombinant SARS-CoV-2 spike (S) protein antigen is in a prefusion conformation and comprises a fragment of a wild-type SARS-CoV-2 protein having the amino acid sequence of SEQ ID NO: 1, wherein the fragment comprises the S1 and S2 domains and includes a double proline substitution at positions 986 and 987 of the wild-type protein and wherein the fragment further comprises a furin cleavage site "GSAS (SEQ ID NO: 5)" at positions 682 to 685 of the wild-type protein and a C-terminal T4 fibritin foldon motif "GYIPEAPRGDQAYVRKDGEWVLLSTFL" (SEQ ID NO: 2).

23. The method of claim 22, wherein the Fc-binding protein is Protein G, Protein A, or a Protein A/G fusion protein.

24. The method of claim 22, wherein the detection agent conjugated to the SARS-CoV-2 spike (S) protein antigen is selected from the group comprising metallic nanoparticles or nanoshells, non-metallic nanoparticles or nanoshells, enzymes, and fluorescent molecules.

25. The method of claim 22, wherein the detection agent comprises nanoparticles or nanoshells of metallic gold.

26. The method of claim 22, wherein the fragment corresponds to residues 14 to 1208 of the wild-type SARS-CoV-2 protein.

* * * * *